United States Patent
Kojoh et al.

(10) Patent No.: US 9,493,523 B2
(45) Date of Patent: Nov. 15, 2016

(54) RNF8-FHA DOMAIN-MODIFIED PROTEIN AND METHOD OF PRODUCING THE SAME

(75) Inventors: Kanehisa Kojoh, Chiba (JP); Shizue Katoh, Chiba (JP); Akira Miyakoshi, Chiba (JP); Mikiko Nakamura, Chiba (JP)

(73) Assignee: GeneFrontier Corporation, Kashiwa (JP)

( * ) Notice: Subject to any disclaimer, the term of this patent is extended or adjusted under 35 U.S.C. 154(b) by 110 days.

(21) Appl. No.: 13/810,025

(22) PCT Filed: May 6, 2011

(86) PCT No.: PCT/JP2011/061009
§ 371 (c)(1),
(2), (4) Date: Feb. 22, 2013

(87) PCT Pub. No.: WO2012/008211
PCT Pub. Date: Jan. 19, 2012

(65) Prior Publication Data
US 2013/0143299 A1 Jun. 6, 2013

(30) Foreign Application Priority Data
Jul. 14, 2010 (JP) .................. 2010-159227

(51) Int. Cl.
*C07K 14/47* (2006.01)
*C12N 9/00* (2006.01)

(52) U.S. Cl.
CPC ............... *C07K 14/47* (2013.01); *C12N 9/93* (2013.01); *C07K 2317/76* (2013.01); *C07K 2317/92* (2013.01); *C07K 2318/20* (2013.01)

(58) Field of Classification Search
None
See application file for complete search history.

(56) References Cited

FOREIGN PATENT DOCUMENTS

JP 2001-500531 A 1/2001
WO WO 98/56915 A2 12/1998
WO WO 2009/039244 A1 3/2009

OTHER PUBLICATIONS

Huen et al, Cell, 2007, 131:901-914 and supplemental data pp. 15-31.*
Mahajan et al. (Biochemistry, 2008, 51:1-18).*
Durocher et al. (Molecular Cell, 2000, 6:1169-1182).*
Ronnmark et al. (European Journal of Biochemistry, 2002, 269:2650-2655).*
Binz (Nature Biotechnology, 2005, 23:1257-1268).*
Kolas et al. (Nature, 2007, 318:1637-1640).*
Ronnmark et al., European Journal of Biochemistry, 2002 269:2647-2655.*
European Patent Office, Communication Pursuant to Article 94(3) EPC in European Patent Application No. 11722934.4 (Mar. 17, 2014).
Bird et al., *Science*, 242: 423-426 (1988).
Gebauer et al., *Current Opinion in Chemical Biology*, 13: 245-255 (2009).
He et al., *Expert Rev. Proteomics*, 2(3): 421-430 (2005).
Holliger et al., *Proc. Natl. Acad. Sci. USA*, 90: 6444-6448 (1993).
Huen et al., *Cell*, 131: 901-914 (2007).
Jendreyko et al., *J. Biol. Chem.*, 278: 47812-47819 (2003).
Kojoh et al., "*In vitro selection from designed protein scaffold library with Ribosome Display on PURE system*," retrieved from Internet on Sep. 2, 2011, at http://www.genefrontier.com/pdf/Poster%20for%20PEGS.pdf (May 9, 2001).
Matsuura et al., *Orig. Life. Evol. Biosph.*, 34: 151-157 (2004).
Marasco et al., *Proc. Natl. Acad. Sci. USA*, 90: 7889-7893 (1993).
Melchionna et al., *J. Mol. Biol.*, 374: 641-654 (2007).
Ohage et al., *J. Mol. Biol.*, 291: 1129-1134 (1999).
Olson et al., *Protein Science*, 16: 476-484 (2007).
Parker et al., *Protein Engineering, Design & Selection*, 18(9): 435-444 (2005).
Proba et al., *J. Mol. Biol.*, 265: 161-172 (1997).
Shimizu et al., *Methods*, 36: 299-304 (2005).
Skerra, Arne, *Curr. Opinion Biotechnol.*, 18: 295-304 (2007).
Ueda et al., *Methods Mol. Biol.*, 607: 219-225 (2010).
Villemagne et al., *Journal of Immunological Methods*, 313: 140-148 (2006).
Visintin et al., *Proc. Natl. Acad. Sci. USA*, 96: 11723-11728 (1999).
Zhou et al., *Molecular Cell*, 6: 751-756 (2000).
Japanese Patent Office, International Search Report in International Patent Application No. PCT/JP2011/061009 (Sep. 21, 2011).
International Bureau of WIPO, International Preliminary Report on Patentability in International Patent Application No. PCT/JP2011/061009 (Jan. 15, 2013).
Kojoh et al., "In vitro selection from Designed Protein Scaffold Library with Ribosome Display on PURE System," poster presentation at PEGS: The Essential Protein Engineering Summit held on May 9-13, 2011 (retrieved from internet at http://www.genefrontier.com/pdf/Poster%20for%20PEGS.pdf on Sep. 2, 2011).
Cambridge Healthtech Institute, Program Guide for PEGS: The Essential Protein Engineering Summit held on May 9-13, 2011, pp. 1, 3, and 22 (2011).
Kojoh et al., "In vitro selection from Designed Protein Scaffold Library with Ribosome Display on PURE System," abstract of poster presentation at PEGS: The Essential Protein Engineering Summit held on May 9-13, 2011 (possibly available Apr. 2011).

* cited by examiner

*Primary Examiner* — Julie Wu
(74) *Attorney, Agent, or Firm* — Leydig, Voit & Mayer, Ltd.

(57) ABSTRACT

Provided is an antigen-binding protein prepared merely by a method of in vitro selection using the RNF8-FHA domain, which has no intramolecular disulfide bond and functions in cells as it is. One to four loops extending from the FHA domain are randomized, and a recognition site for a target molecule is artificially created on the FHA domain surface to construct an RNF8-FHA domain library. Using the library, an antigen-binding protein is efficiently selected in vitro.

8 Claims, 11 Drawing Sheets

Fig. 2

```
                                                                                                    100
ggCgagccTggcttcttcgtcacCggagaccgcgccggtggccgCTCAtggtgcctgcgCcgCgtgggCatgagcgccggCtggctgctTctCgaGgatggTtgcgaAgtTacCgtTggT
 G  E  P  G  F  F  V  T  G  D  R  A  G  G  R  S  W  C  L  R  R  V  G  M  S  A  G  W  L  L  L  E  D  G  C  E  V  T  V  G
┌──────┬──────┐   ┌──────┬──────────────┐                                                                      ┌──────┐
│Loop1 │Loop1'│   │Loop2'│    Loop2     │                              200                                     │Loop3 │
cgtggattt ggtgtcac Ctacca Gctggtatcaaaa atctgcccgctgatgatttctcgt aaccac tgCgttCtTaagcaAaatcctgagggccaatggacCattatggacaacaagagt
 R  G  F  G  V  T  Y  Q  L  V  S  K  I  C  P  L  M  I  S  R  N  H  C  V  L  K  Q  N  P  E  G  Q  W  T  I  M  D  N  K  S
└──────┴──────┘   └──────┴──────────────┘                                                                      └──────┘
┌──────┐                                 300                              ┌─────────────┬──────────┐
│Loop3 │                                                                  │   Loop4     │  Loop4'  │
ctgaatgg tgtttggctgaacCgAgcgcgCctggaacctttGCgCgtctatAGcattcatcagggTgactacatccaacttgg tgtgcctctggaaaataaa gagaatgcCga tatgaa
 L  N  G  W  L  N  R  A  R  L  E  P  L  R  V  Y  S  I  H  Q  G  D  Y  I  Q  L  G  V  P  L  E  N  K  E  N  A  E  Y  E
└──────┘                                                                  └─────────────┴──────────┘
            400
tatgaagttacCgaagaagactgggaAacCatTtatccttgtcttAGcccTaagaatgaTcaaatgatTgaaaaGaat
 Y  E  V  T  E  E  D  W  E  T  I  Y  P  C  L  S  P  K  N  D  Q  M  I  E  K  N
```

RNF8-FHA DOMAIN-MODIFIED PROTEIN AND METHOD OF PRODUCING THE SAME

CROSS-REFERENCE TO RELATED APPLICATIONS

This patent application is the U.S. national phase of International Patent Application No. PCT/JP2011/061009, filed on May 6, 2011, which claims the benefit of Japanese Patent Application No. 2010-159227, filed on Jul. 14, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 36,398 bytes ASCII (Text) file named "712036SequenceListing.txt," created Jan. 9, 2013.

TECHNICAL FIELD

The present invention relates to an E3 ubiquitin ligase RNF8 FHA domain-modified protein that exhibits a new binding affinity for a predetermined antigen as a result of a modification of the FHA domain, and a method of preparing the same.

BACKGROUND ART

Antibody affinity and specificity are widely applied in a broad range of fields, including therapeutic applications, diagnoses, and reagents. With recent years' advances in antibody engineering, miniaturized antibodies in a wide variety of forms, such as scFv (single chain Fv) and diabody have been reported [Bird et al., Science (1988), vol. 242, pp. 423-426; Holliger et al., Proc. Natl. Sci. USA (1993), vol. 90, pp. 6444-6448]. Furthermore, artificial antibody molecules that are smaller and more stable than antibodies have been developed [Skerra, Curr. Opin. Biotechnol. (2007), vol. 18, pp. 295-304].

For example, JP-T-2001-500531 discloses an artificial antibody of a fibronectin III type domain that mimics the CDR (complementarity determining region) of an antibody. This artificial antibody has an antigen recognition site artificially created on the surface of a protein by randomizing flexible loops on the protein surface.

RNF8 is an E3 ubiquitin ligase having a RING-Finger domain and an FHA domain, and is known to be involved in responses to DNA damage. Conformational analysis showed that the FHA domain of RNF8 (PDB code: 2PIE, 2CSW) has an Immunoglobulin(Ig)-like structure (β sandwich structure) with five loops (two long loops and three short loops) on the protein surface (FIG. 1). Also, the binding to the binding partner MCD1 has been shown to occur via the two long loops in the FHA domain. This binding pattern is similar to the antigen recognition pattern of antibody; the FHA domain of RNF8 is expected to have a suitable structure for development of artificial antibody molecules.

Also, RNF8 is an intracellular protein and an artificial antibody derived from RNF8 is therefore expected to work as a highly functional intrabody (intracellularly expressed antibody). An intrabody is defined as an antibody (primarily scFv) that works within cells to bind to an intracellular protein as a target thereof. Intrabodies have been developed for therapeutic uses for a wide variety of disease, for example, AIDS, cancers, Alzheimer's disease, Parkinson's disease, and Huntington's disease.

Furthermore, intrabodies are effective in knocking out intracellular targets. RNAi is a generally known knock-out form of intracellular target. However, RNAi is not applicable to analyzing post-translationally modified targets because the gene is knocked out as it is, and also because the half-life of the intracellular RNA is short. Intrabodies have longer half-lives in cells than those of RNA, and can knock out at the protein level. For this reason, intrabodies make it possible to solve the above-described problem with RNAi [Zhou et al., Mol. Cell. (2000), vol. 6, pp. 751-756; Jendreyko et al., J. Biol. Chem. (2003), vol. 278, pp. 47812-47819; Melchionna et al., J. Mol. Biol. (2007), vol. 374, pp. 641-654].

However, the binding activity often decreases or disappears completely when the antibody is expressed as an intrabody in cells under reducing environmental conditions due to the disruption of disulfide bonds in their molecular structure.

Initial attempts to solve this problem included the development of an antibody deprived of intramolecular cysteine involved in disulfide bonds [Proba et al., J. Mol. Biol. (1997), vol. 265, pp. 161-172] and an antibody with increased stability [Ohage et al., J. Mol. Biol. (1999), vol. 291, pp. 1129-1134]. As a method of preparing a functional antibody in cells more effectively, a method of direct selection of scFv in cells was developed [Visintin et al., Proc. Natl. Acad. Sci. USA (1999), vol. 96, pp. 11723-11728]. However, selection systems using cells have limitations with regard to ligation efficiency of antibody library onto the vector and cell transformation efficiency. For this reason, it is difficult to apply selection systems using cells to a library with greater diversity. Therefore, combinations with another method such as phage display or ribosome display, and a method of validation for selected scFv have been proposed.

DOCUMENT LIST

Patent Document patent document 1: JP-A-2001-500531

Non-Patent Documents non-patent document 1: Bird et al, Science (1988), vol. 242, p423-426
non-patent document 2: Holliger et al, Proc. Natl. Sci. USA (1993), vol. 90, p 6444-6448
non-patent document 3: Skerra, Curr Opin Biotechnol (2007), vol. 18, p 295-304
non-patent document 4: Zhou et al, Mol. Cell. (2000), vol. 6, p751-756,
non-patent document 5: Jendreyko et al, J. Biol. Chem (2003), vol. 278, p 47812-47819
non-patent document 6: Melchionna et al, J. Mol. Biol (2007), vol. 374, p 641-654
non-patent document 7: Proba et al, J. Mol. Biol (1997), vol. 265, p 161-172
non-patent document 8: Ohage et al, J. Mol. Biol (1999), vol. 291, p 1129-1134
non-patent document 9: Visintin et al, Proc. Natl. Acad. Sci. USA (1999), vol. 96, p 11723-11728

SUMMARY OF THE INVENTION

Problems to be Solved by the Invention

It is an object of the present invention to efficiently produce an RNF8-FHA domain-modified protein that functions as an artificial antibody and does not lose its binding activity even when expressed as an intrabody in cells, in vitro.

Means of Solving the Problems

Because the RNF8-FHA domain is a protein that does not have any intramolecular disulfide bond and functions as it is in cells, the above-described optimization is unnecessary; it is possible to efficiently prepare a functional antibody merely by in vitro general selection.

In a first aspect, the present invention relates to a method of producing an artificial antibody. This method comprises the step of preparing randomized-loop polypeptides obtained by randomizing a loop in the E3 ubiquitin ligase RNF8-FHA domain, and the step of selecting an antigen-binding protein from among the randomized-loop polypeptides.

The E3 ubiquitin ligase RNF8-FHA domain is a polypeptide that does not have any intramolecular disulfide bond and fulfills its functions in cells. The randomized-loop polypeptide of the present invention makes it possible to prepare an antigen-binding protein merely by general in vitro selection using the RNF8-FHA domain.

Specifically, one to four loops extending from the FHA domain are randomized, and a recognition site for the subject target molecule is artificially created on the surface of the FHA domain. An RNF8-FHA domain library comprising such randomized-loop polypeptides is constructed. Then, an antigen-binding protein is efficiently selected in vitro.

The method of constructing an RNF8-FHA domain library is hereinafter described in further detail. An artificial antibody library is generated by introducing random sequences into any one or two or more loops selected from among a loop consisting of the 41 st-43 rd amino acid residues of the RNF8 protein shown by SEQ ID NO:1 (Loop 1), a loop consisting of the 53 rd-60th amino acid residues of the RNF8 protein shown by SEQ ID NO:1 (Loop 2), a loop consisting of the 80th-82 nd amino acid residues of the RNF8 protein shown by SEQ ID NO:1 (Loop 3), and a loop consisting of the 109th-114th amino acid residues of the RNF8 protein shown by SEQ ID NO:1 (Loop 4), wherein the random sequences have the same number of residues as those in the respective loops. It is possible to obtain binding molecules for a wide variety of antigens such as proteins, peptides, small molecules, and sugar chains from this library. It should be noted, however, that the polypeptide having the amino acid sequence shown by SEQ ID NO:1 into which random sequences are to be introduced may have one or several amino acid residues deleted, substituted, inserted, or added. That is, in place of the polypeptide having the amino acid sequence shown by SEQ ID NO:1 in the foregoing explanation, a randomized-loop polypeptide consisting of an amino acid sequence wherein one or several amino acid residues are deleted from, substituted for, inserted into, or added to, a region of SEQ ID NO:1 other than (a) the 41 st-43 rd amino acid residues, (b) the 53 rd-60th amino acid residues, (c) the 80th-82 nd amino acid residues, and (d) the 109th-114th amino acid residues, may be obtained.

In a further aspect of the present invention, an artificial antibody library is also generated by introducing random sequences into any one or two or more loops selected from among a loop consisting of the 41 st-46th amino acid residues of the RNF8 protein shown by SEQ ID NO:1 (Loop 1'), a loop consisting of the 49th-62 nd amino acid residues of the RNF8 protein shown by SEQ ID NO:1 (Loop 2'), a loop consisting of the 78th-83 rd amino acid residues of the RNF8 protein shown by SEQ ID NO:1 (Loop 3'), and a loop consisting of the 108th-118th amino acid residues of the RNF8 protein shown by SEQ ID NO:1 (Loop 4'), wherein the random sequences have the same number of residues as those in the respective loops. It is possible to obtain binding molecules for a wide variety of antigens such as proteins, peptides, small molecules, and sugar chains from this library. It should be noted, however, that the polypeptide having the amino acid sequence shown by SEQ ID NO:1 into which random sequences are to be introduced may have one or several amino acid residues deleted, substituted, inserted, or added. That is, in place of the polypeptide having the amino acid sequence shown by SEQ ID NO:1 in the foregoing explanation, a randomized-loop polypeptide consisting of an amino acid sequence wherein one or several amino acid residues are deleted from, substituted for, inserted into, or added to, a region of SEQ ID NO:1 other than (a) the 41 st-46th amino acid residues, (b) the 49th-62 nd amino acid residues, (c) the 78th-83 rd amino acid residues, and (d) the 108th-118th amino acid residues, may be obtained.

An example of the above-described randomized-loop polypeptide is a polypeptide having a random sequence introduced into a loop in the E3 ubiquitin ligase RNF8-FHA domain. An example of the number of amino acid residues of the introduced random sequence is 3-12 residues. In the present invention, it is preferable that a random sequence with a length like this be introduced.

Subsequently, an antigen-binding protein is selected from the artificial antibody library. An example method for selecting an antigen-binding protein is in vitro selection. Examples of methods of in vitro selection include phage display, ribosome display, mRNA display, yeast surface display, and bacteria display. These methods are generally known as in vitro selection systems.

Ribosome display is a method wherein a ribosome-peptide-mRNA complex is formed in an in vitro translation system, and a protein that encodes a peptide having a particular function is selected. In this method, preference is given to a ribosome display utilizing the PURE system [Shimizu et al. (2005), Methods, vol. 36, pp. 299-304], which is a reconstituted protein synthesis system that has been reported to have higher selectivity than the common ribosome display using *Escherichia coli* extract.

In a second aspect, the present invention relates to an artificial antibody or a complex of an artificial antibody and an antigen, produced or selected by the method described above. This artificial antibody is preferably an intrabody. Examples of the antigen protein in the complex of an artificial antibody and an antigen protein are Erk2(extracellular signal-regulated kinase 2) and Trx(Thioredoxin).

A specific example of artificial antibody is an artificial antibody consisting of the amino acid sequence shown by any one of SEQ ID NO:21 to 42. The artificial antibody of the present invention may be an artificial antibody consisting of the amino acid sequence shown by any one of ID NO:21 to 42 wherein one or several amino acid residues are deleted from, substituted for, inserted into, or added to, a region other than (a) the 41 st-43 rd amino acid residues, (b) the 53 rd-60th amino acid residues, (c) the 80th-82 nd amino acid residues, and (d) the 109th-114th amino acid residues. These artificial antibodies are preferably intrabodies.

An example of the above-described randomized-loop polypeptide is a polypeptide having a random sequence introduced into any one or two or more regions of (a) the 41 st-43 rd amino acid residues, (b) the 53 rd-60th amino acid residues, (c) the 80th-82 nd amino acid residues, and (d) the 109th-114th amino acid residues of the amino acid sequence shown by SEQ ID NO:1. An example of introducing a random sequence is to replace the above-described loop region with the random sequence.

An example of the above-described randomized-loop polypeptide is a polypeptide having a random sequence introduced into any one or two or more regions of (a) the 41 st-46th amino acid residues, (b) the 49th-62 nd amino acid residues, (c) the 78th-83 rd amino acid residues, and (d) the 108th-118th amino acid residues of the amino acid sequence shown by SEQ ID NO:1. An example of introducing a random sequence is to replace the above-described loop region with the random sequence.

Effect of the Invention

According to the present invention, modified proteins can be utilized as artificial antibodies that make it possible to obtain binding proteins for a wide variety of antigens.

When intracellular proteins are used as the antigens, the binding proteins that recognize the same can be allowed to work as intrabodies in cells. For example, the binding proteins can find a broad range of totally new applications, from basic biochemical experiments such as inhibition of protein-protein interactions, imaging of targets in living cells, and control of localization of target molecule, to applications to protein-protein interaction analysis (proteomics analysis), reagents, certain diagnoses, and therapeutic drugs.

BRIEF DESCRIPTION OF THE DRAWINGS

FIG. 2 shows the amino acid sequence of the RNF8-FHA domain.

MODES FOR EMBODYING THE INVENTION

Figure 1:
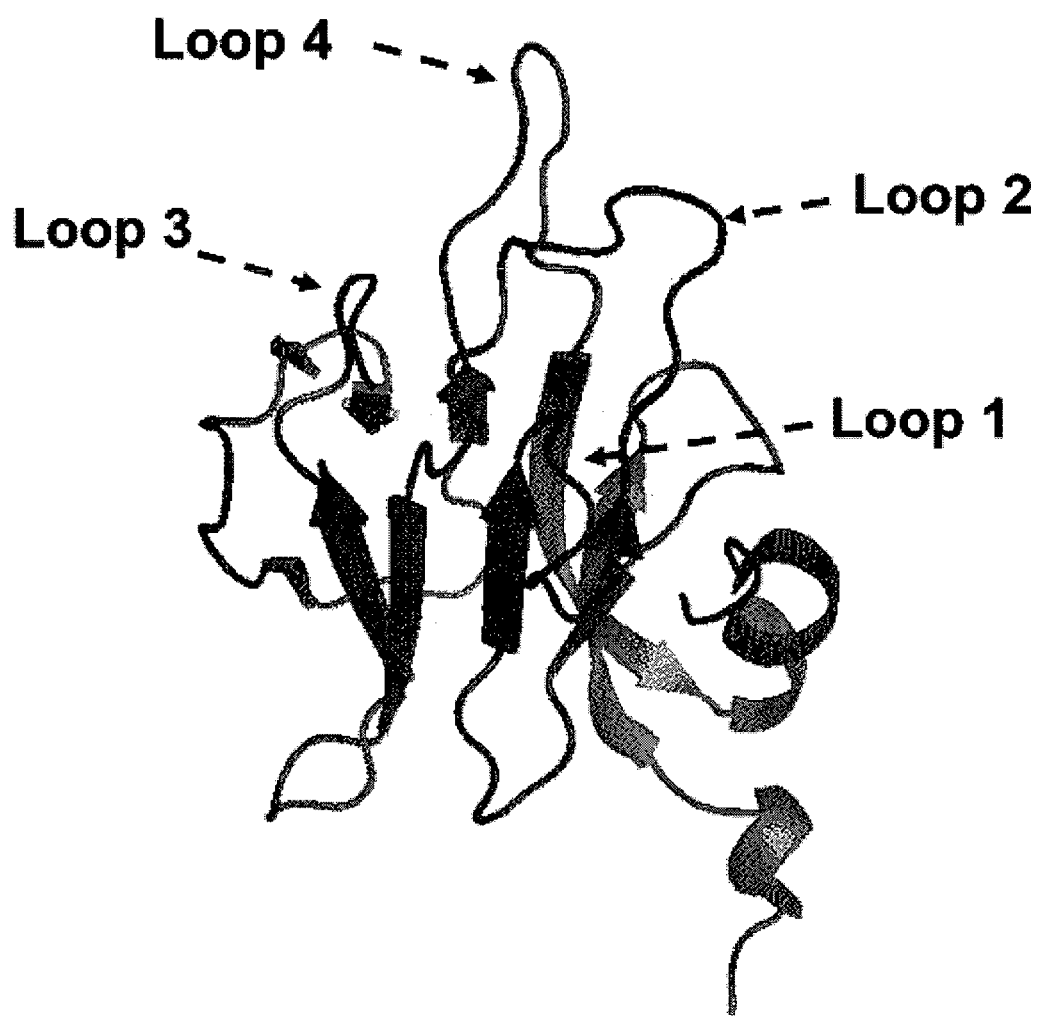
FIG. 1 shows the schematic drawing of the RNF8-FHA domain structure.

Described below is how to construct an RNF8-FHA domain library in the present invention. In this method, one to four loops extending from the FHA domain are first randomized, and a recognition site for the subject target is artificially created on the surface of the FHA domain.

In this method, an artificial antibody library is generated by introducing random sequences into any one or two or more loop regions selected from among a loop consisting of the 41 st-43 rd amino acid residues of the RNF8 protein shown by SEQ ID NO:1 (Loop 1), a loop consisting of the 53 rd-60th amino acid residues of the RNF8 protein shown by SEQ ID NO:1 (Loop 2), a loop consisting of the 80th-82 nd amino acid residues of the RNF8 protein shown by SEQ ID NO:1 (Loop 3), and a loop consisting of the 109th-114th amino acid residues of the RNF8 protein shown by SEQ ID NO:1 (Loop 4). It should be noted, however, that the polypeptide having the amino acid sequence shown by SEQ ID NO:1 into which random sequences are to be introduced may have one or several amino acid residues deleted, substituted, inserted, or added. That is, in place of the polypeptide having the amino acid sequence shown by SEQ ID NO:1 in the foregoing explanation, a randomized-loop polypeptide comprising (or consisting of) an amino acid sequence wherein one or several amino acid residues are deleted from, substituted for, inserted into, or added to, a region of SEQ ID NO:1 other than (a) the 41 st-43 rd amino acid residues, (b) the 53 rd-60th amino acid residues, (c) the 80th-82 nd amino acid residues, and (d) the 109th-114th amino acid residues, may be obtained.

In a further aspect of the present invention, in this method, an artificial antibody library is also generated by introducing random sequences into any one or two or more loop regions selected from among a loop consisting of the 41 st-46th amino acid residues of the RNF8 protein shown by SEQ ID NO:1 (Loop 1'), a loop consisting of the 49th-62 nd amino acid residues of the RNF8 protein shown by SEQ ID NO:1 (Loop 2'), a loop consisting of the 78th-83 rd amino acid residues of the RNF8 protein shown by SEQ ID NO:1 (Loop 3'), and a loop consisting of the 108th-118th amino acid residues of the RNF8 protein shown by SEQ ID NO:1 (Loop 4'). It should be noted, however, that the polypeptide having the amino acid sequence shown by SEQ ID NO:1 into which random sequences are to be introduced may have one or several amino acid residues deleted, substituted, inserted, or added. That is, in place of the polypeptide having the amino acid sequence shown by SEQ ID NO:1 in the foregoing explanation, a randomized-loop polypeptide comprising (or consisting of) an amino acid sequence wherein one or several amino acid residues are deleted from, substituted for, inserted into, or added to, a region of SEQ ID NO:1 other than (a) the 41 st-46th amino acid residues, (b) the 49th-62 nd amino acid residues, (c) the 78th-83 rd amino acid residues, and (d) the 108th-118th amino acid residues, may be obtained.

An example of introducing a random sequence is to replace a loop region (surrounded by a solid square in FIG. 2) or a loop region selected from among loops 1'-4' (surrounded by a dashed square in FIG. 2) with the random sequence. Examples of random sequences are random sequences having 3-12 residues. A preferable case of introducing a random sequence is to replace with a random sequence having the same number of residues as the number of residues in the region where the random sequence is to be introduced. To obtain such a randomized-loop polypeptide, a random oligonucleotide may be introduced into the region corresponding to the loop region in the DNA of the polypeptide shown by SEQ ID NO:1. Examples of random oligonucleotides are the NNK sequence, the NNS sequence and the NNY sequence, wherein N stands for adenine (A), guanine (G), cytosine (C), or thymine (T); K for guanine (G) or thymine (T); S for cytosine (C) or guanine (G); Y for cytosine (C) or thymine (T). A random nucleotide may be generated by a publicly known method. A method of introducing a random oligonucleotide into DNA or RNA is also publicly known.

Next, the RNA incorporating a random oligonucleotide, corresponding to the above-described loop (random loop) is transcribed to obtain a transcription product. The transcription step is publicly known in the field of biotechnology. Therefore, the transcription step can be carried out on the basis of a publicly known method.

The transcription product thus obtained is translated in vitro. Thereby, an RNFB-FHA domain library can be obtained.

Next, an antigen-binding protein is selected from the RNF8-FHA domain library. Useful methods for selecting an antigen-binding protein include methods generally known as in vitro selection, such as phage display, ribosome display, mRNA display, yeast surface display, and bacterial display. Preference is given to a ribosome display based on the PURE system, a reconstructed protein synthesis system with higher selectivity than the common ribosome display using *Escherichia coli* extract. The PURE system is a cell-free translation system wherein the factors necessary for the translation are separately prepared and reconstituted. The PURE system has been reported to have high selection efficiency because of little contamination with nucleases and proteases, which can reduce the efficiency of ribosome display [Villemagne et al., (2006) J. Immunol. Methods, vol. 313, pp. 140-148].

A cell-free translation system has an energy regeneration system and at least one kind of amino acid. An energy regeneration system means an element involved in the regeneration of energy sources that are necessary for protein synthesis, such as ATP and GTP. Examples of energy regeneration system substances include enzymes involved in ATP regeneration (creatine kinase, pyruvate kinase) and substrates thereof (creatine phosphate, phosphoenol pyruvate and the like). The cell-free translation system comprises at least one kind of amino acid, preferably all the 20 kinds of amino acids occurring in nature. The cell-free translation system may further comprise a non-natural amino acid. The cell-free translation system may comprise, for example, a buffer solution (for example, HEPES potassium, Tris-acetate and the like), various salts, a surfactant, a RNA polymerase (T7, T3, and SP6 RNA polymerase and the like), a chaperone protein (DnaJ, DnaK, GroE, GroEL, GroES, HSP70 and the like), an RNA (mRNA, tRNA and the like), a protease inhibitor, or a (ribo)nuclease inhibitor.

Using these methods, the above-described random oligonucleotide transcription product is translated in vitro. An example of this translation step is to translate the transcription product in vitro using a cell-free translation system. This step results in the construction of a ribosome-peptide-mRNA complex.

By binding the ribosome-peptide-mRNA complex and a predetermined antigen, it is possible to select the mRNA of a peptide that binds to the antigen in vitro (in vitro selection). The antigen may be any one of proteins, peptides, small molecules, sugar chains and the like. Here, previously labeling the antigen with biotin makes it possible to screen for an antigen-binding peptide by ELISA as described below. This labeling step is publicly known in the field of biotechnology. Therefore, the labeling step can be carried out on the basis of a publicly known method.

The mRNA selected by the method above is recovered and reverse-transcribed into a cDNA, which is amplified by a PCR reaction, whereby a gene for ribosome display for the second and subsequent rounds can be reconstructed. The ribosome display is preferably performed in four rounds or more.

The gene recovered by the several rounds of ribosome display and in vitro selection may be subcloned into an expression vector, and the subclones obtained are screened by ELISA, whereby it is possible to express and purify an RNF8-FHA domain-modified protein (antigen-binding protein) of high binding affinity for the antigen. These steps are publicly known in the field of biotechnology, and can therefore be performed on the basis of a publicly known method.

As stated above, a preferred utilization of the present invention represents a method wherein a library of RHF8-FHA domain-modified proteins is generated, and an RHF8-FHA domain-modified protein of high binding affinity for an antigen (antigen-binding protein) is selected using a ribosome display in vitro.

The present invention is hereinafter described specifically by means of the following examples, to which, however, the present invention is not limited. Modifications made within a range obvious to those skilled in the art are also included in the scope of the invention.

EXAMPLES

Construction of RNF8-FHA Domain Library

Based on the conformation of the FHA domain of RNF8 (FIG. 1, PDB code: 2PIE), an RNF8 library comprising four randomized (NNS) loops of the FHA domain of RNF8 (FIG. 2, SEQ ID NO:1) was designed and chemically synthesized as a fragment 140 bases or less (FASMAC). The regions to be randomized were the regions of the RNF8 protein surrounded with squares in FIG. 2, which consist of the 41 st-43 rd amino acid residues, the 53 rd-60th amino acid residues, the 80th-82 nd amino acid residues, and the 109th-114th amino acid residues, respectively. For the library genes, socalled optimal codons (capitalized in FIG. 2) were used for the sake of high protein expression. Also a 5' UTR sequence comprising a T7 promoter and the SD sequence with the FLAG sequence added to the 3' end thereof, which are required in performing ribosome display, was chemically synthesized (FASMAC). Each underlined region indicates a region complemented (overlapped) by each oligo-DNA.

N-Term (SEQ ID NO: 2:
GACTATAAAGATGACGATGACAAAggcgagcctggcttcttcgtcaccgg agaccgcgccggtggccgctcatggtgcctgcgccgcgtgggcatgagcg ccggctggctgcttctcgaggatggtTGCgaagttac)

C-Term (SEQ ID NO: 3:
cCgaagaagactgggaAacCatTtatccttgtcttAGcccTaagaatgaT caaatgatTgaaaaGaatGAATTCggtggcagcggaggtgaatatcaagg ccaatcgtctgac)

LOOPs 1 & 2 (SEQ ID NO: 4:
ctTctCgaGgatggTTGCgaAgtTacCgtTggTNNSNNSNNSggtgtcac

CtaccaGctggtatcaaaannsnnsnnsnnsnnsnnsnnsaaccact gCgttCtTaagcaAaatcctgag)

LOOP 3 (SEQ ID NO: 5:
ccactgCgttCtTaagcaAaatcctgagggccaatggacCattatggaca acaagNNSNNSNNSggtgtttggctgaacCgAgcgcgCctggaacctttG CgCgtctatAGcattcatcagggTgac)

LOOP 4 (SEQ ID NO: 6:
GCgCgtctatAGcattcatcagggTgactacatccaacttggTNNSNNSN

NSNNSNNSNNSgagaatgcCgagtatgaatatgaagttacCgaagaagac tgggaAaccatttatcc)

5' UTR (SEQ ID NO: 7:
gaaattaatacgactcactatagggagaccacaacggtttccctctagaa ataattttgtttaactttaagaaggagatataccaatggactataaagat gacgatgacaaa)

A partial sequence of the gene III (g3p) of the M13 phage (amino acid residues at 220-326 positions) was amplified with KOD Plus DNA Polymerase (TOYOBO) by a PCR reaction (denaturation: 94° C., 10 seconds; annealing: 58° C., 30 seconds; elongation: 68° C., 60 seconds; 25 cycles) with a M13KO7-derived phage genome as the template using the primer g3p (SEQ ID NO:8: GAATATCAAGGC-CAATCGTCTGAC) and the primer g3p-SecMstop (SEQ ID NO:9: CTCGAGTTATTCATTAGGTGAGGCGTT-GAGGGCCAGCACGGATGCCTTGCGCCTGGCTTATC CAGACGGGCGTGCTGAATTTTGCGCCGGAAACGT-CACCAATGAAAC), and then purified using the QIAquick PCR purification kit (QIAGEN).

A PCR reaction mixture containing each chemically synthesized gene fragment (5'UTR, N-Term, Loops 1&2, Loop 3, Loop 4, C-term) and the g3p gene, 1 pmol each, and KOD Plus DNA Polymerase (TOYOBO) (500 µL in total), was prepared; 15 cycles of a PCR reaction (denaturation: 94° C., 10 seconds; annealing: 58° C., 30 seconds; elongation: 68° C., 60 seconds) was carried out, after which 10 pmol of a 5' primer (SEQ ID NO:10: gaaattaatacgactcactatagggagacca-caacggtttccctctag), 10 pmol of the primer SecMstop (SEQ ID NO:11: ggattagttattcattaggtgaggcgttgagg), and 1 µL of KOD Plus DNA Polymerase were further added to the reaction mixture (50 µL×10 vials), and 10 cycles of a PCR reaction (denaturation: 94° C., 10 seconds; annealing: 58° C., 30 seconds; elongation: 68° C., 60 seconds) was carried out. After a band of all genes connected together was confirmed by electrophoresis using 1% agarose, the band was cut out and purified using the MiniElute Gel Extraction Kit (QIAGEN) to finally obtain a gene library comprising the random sequences.

In Vitro Transcription

One microgram of the purified gene library DNA was treated with 20 µL of an in vitro transcription kit (Ribomax™ Large Scale RNA Production System-T7, Promega) to obtain an mRNA, which was purified through a column (RNeasy mini column, QIAGEN).

In Vitro Translation Using a Cell-Free Translation System (Construction of Ribosome-Peptide-mRNA Complex)

A cell-free translation system which is a protein synthesis reaction reagent (PURE system) was generated as reported [Shimizu et al. (2005), Methods, vol. 36, pp. 299-304]. 10 pmol of the mRNA library was added to the prepared reaction mixture (100 µl), and this mixture was incubated at 37° C. for 30 minutes. 500 µL of an ice-cooled wash buffer solution [50 mM Tris-OAc, pH 7.5, 150 mM NaCl, 50 mM Mg(OAc)$_2$, 0.5% Tween 20, 1 µg/mL Saccharomyces cerevisiae total RNA (Sigma)] was added, and 500 µL of a blocking buffer solution [50 mM Tris-OAc, pH 7.5, 150 mM NaCl, 50 mM mg(OAc)$_2$, 0.5% Tween 20, 100 µg/mL Saccharomyces cerevisiae total RNA (Sigma), 5% Super-Block (PIERCE)] was added. Dynabeads MyOne streptavidin T1 magnetic beads (100 µL of slurry, Invitrogen), previously blocked with 5% SuperBlock at 4° C. overnight, were twice washed with 500 µL of the wash buffer solution using the MagneSphere Magnetic Separation Stand (Promega), after which the entire volume of the post-translational reaction mixture (ribosome display library solution) was added, and a treatment for pre-adsorption to the magnetic beads and streptavidin was performed at 4° C. for 60 minutes. The resulting supernatant was recovered using the MagneSphere Magnetic Separation Stand (Promega).

Biotinylation of Antigen Proteins

Each of antigen proteins purchased from Sigma (human Erk2 and Escherichia coli thioredoxin: Trx) was biotinylated per the standard protocol for the EZ-Link NHS-PEO$_4$-Biotin (PIERCE). For each biotinylated antigen protein, biotinylation was confirmed by the band mobility shift by SDS-PAGE; their concentrations were determined using the BCA Protein Assay Kit (PIERCE).

In Vitro Selection

Dynabeads MyOne streptavidin T1 magnetic beads (100 µL of slurry, Invitrogen), previously blocked with 5% SuperBlock at 4° C. overnight, was twice washed with 500 µl of wash buffer solution using the MagneSphere Magnetic Separation Stand (Promega), after which 100 nmol of biotinylated antigen protein was added and immobilized onto the magnetic beads at 4° C. Thirty (30) minutes later, the beads were washed with 500 µL of the wash buffer solution three times using the MagneSphere Magnetic Separation Stand (Promega), after which the translation reaction mixture after the pre-adsorption treatment was added to the recovered magnetic beads, and the mixture was stirred at 4° C. by rotation for 1 hour. The supernatant was discarded using the MagneSphere Magnetic Separation Stand (Promega), 1 mL of the wash buffer solution was added to the recovered magnetic beads, and the mixture was stirred at 4° C. by rotation for 5 minutes. After repeating this operation in 30 cycles, 100 µL of an elution buffer solution (50 mM Tris-OAc, pH 7.5, 150 mM NaCl, 50 mM EDTA) was added to the recovered magnetic beads, and this mixture was allowed to stand at 4° C. for 10 minutes, whereby the complex was released from the magnetic beads. The supernatant was recovered using the MagneSphere Magnetic Separation Stand (Promega), and the mRNA was recovered using the RNeasy Micro (QIAGEN) and purified.

RT-PCR

The recovered mRNA was converted to cDNA using the Transcription High Fidelity cDNA Synthesis Kit (Roche), after which RT-PCR (250 µL in total, denaturation: 94° C., 10 seconds; annealing: 58° C., 30 seconds; elongation: 68° C., 60 seconds; 35 cycles) was performed using the KOD Plus DNA Polymerase. The primers used are shown below.

Reverse transcription reverse primer: C-term R
(SEQ ID NO: 12:
GTCAGACGATTGGCCTTGATATTC)

PCR primers: 5' primer (SEQ ID NO: 10:
gaaattaatacgactcactatagggagaccacaacggtttccctctag)
and C-term R (SEQ ID NO: 12:
GTCAGACGATTGGCCTTGATATTC)

After the RT-PCR, the reaction mixture was electrophoresed with 1% agarose; a band of the corresponding size was cut out and purified using the MiniElute Gel Extraction Kit (QIAGEN).

Reconstruction of Gene for Ribosome Display

The gene for ribosome display for the second and subsequent rounds was reconstructed as described below. A PCR reaction mixture containing the purified gene after RT-PCR, 5'UTR, and the g3p gene, each 1 pmol, 10 pmol of the 5' primer (SEQ ID NO:10: gaaattaatacgactcactatagggagacca-caacggtttccctctag), 10 pmol of the primer SecMstop (SEQ ID NO:11: ggattagttattcattaggtgaggcgttgagg), and KOD Plus DNA Polymerase (TOYOBO) (250 µL in total), was prepared and subjected to 15 cycles of a PCR reaction (denaturation: 94° C., 10 seconds; annealing: 58° C., 30 seconds; elongation: 68° C., 60 seconds), after which a band of all genes connected together was identified by electrophoresis using 1% agarose, and then cut out and purified using the MiniElute Gel Extraction Kit (QIAGEN).

Subcloning

Figure 3:
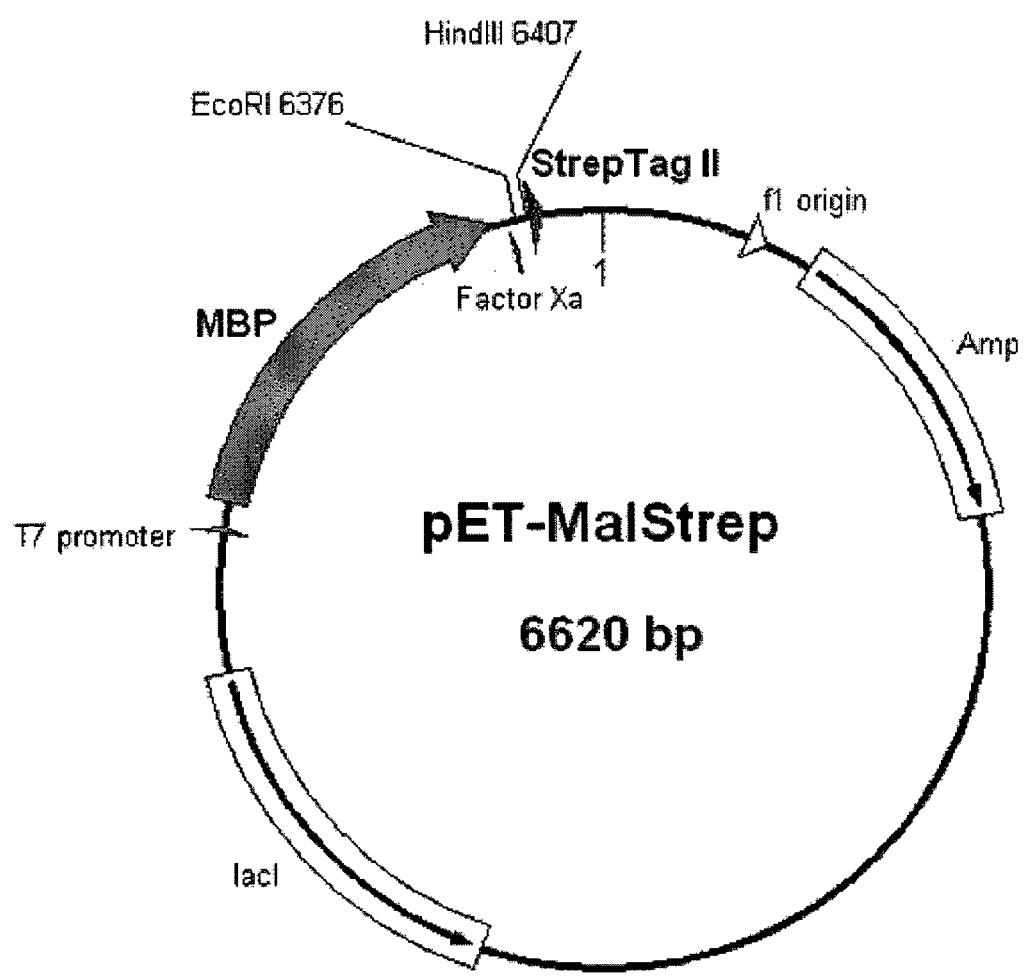
FIG. 3 shows an *Escherichia coli* protein expression vector incorporating the RNF8-FHA gene.

After four rounds, the recovered gene was cloned into the *Escherichia coli* expression vector pET-MalStrep (FIG. 3). Specifically, the four rounds of RT-PCR were followed by a PCR using a reaction mixture containing the primer Eco1-(-M)-FLAG_F incorporating EcoRI on the 5' side (SEQ ID NO:13: CCgaattcGACTATAAAGATGACGAT-GACAAAggC), the primer RNF8-Hind3_R incorporating HindIII on the 3' side (SEQ ID NO:14: ggAAGCTTat-tCttttcAatcatttgAtcattc), and KOD Plus DNA Polymerase (TOYOBO) (100 µL in total). The PCR reaction was subjected to 20 cycles of amplification (denaturation: 94° C., 10 seconds; annealing: 58° C., 30 seconds; elongation: 68° C., 60 seconds), after which the gene was purified using the QIAquick PCR purification kit (QIAGEN). One microgram of the purified gene and the expression vector were treated with the restriction endonuclease EcoRI-HindIII at 37° C. for 1 hour, and the corresponding band was confirmed by electrophoresis using 1% agarose, after which the band was cut out and purified using the MiniElute Gel Extraction Kit (QIAGEN). The insert gene and the vector gene were mixed in a 3:1 molar ratio and reacted using the LigaFast Rapid DNA Ligation Kit (Promega) at room temperature for 30 minutes, after which *Escherichia coli* BL21(DE3) competent cells, which had been previously prepared (Z-competent *E. Coli* Transformation Buffer Set: ZYMO RESEARCH), were transformed therewith, and the cells were cultured on an LB agar plate containing ampicillin (final concentration 50 µg/mL) at 37° C. overnight.

Primary Screening for Antigen-Binding Protein by ELISA

After overnight culture, 95 single colonies were inoculated from the LB agar plate to 100 µL of a 2xYT medium containing ampicillin (final concentration 50 µg/mL), and cultured at 37° C. for 3-5 hours ($OD_{600}$=0.5-0.8), after which IPTG (final concentration 0.1 mM) was added, and the cells were cultured at 25° C. overnight. 90 µL of PBS and 40 µL of a lysis reagent (20 µL of BugBuster Protein Extraction Reagent: Novagen, 20 µL of 2.5 mg/mL Lysozyme solution) were added to 10 µL of the cultured *Escherichia coli* solution, and the cells were lysed at room temperature for 1 hour. 40 µL of 12.5% skimmed milk in PBS was added to the lysed solution, and blocking was performed at room temperature for 1 hour. Concurrently, a 384-well plate, to which an antigen protein had been immobilized at 100 ng/20 µL per well at 4° C. overnight, was twice washed with 100 µL of PBS, 100 µL of 5% skimmed milk in PBS was added, and blocking was performed at room temperature for 1 hour, after which the plate was twice washed with 100 µL of PBS to obtain an antigen-immobilized plate; 20 µL of the blocked *Escherichia coli* extract was added to the plate, and the extract was gently stirred at room temperature using a plate mixer. One hour later, the plate was washed with 100 µL of PBS five times, 20 µL (1:2000 dilution) of an anti-FLAG M2-HRP conjugate (Sigma) was added, and the mixture was gently stirred at room temperature on a plate mixer for 1 hour. Furthermore, the plate was washed with 100 µL of PBS five times, and detection was achieved using 20 µL of a chromogenic substrate (0.4 mg/mL 3,3',5,5'-Tetramethyl-benzidine, 0.01% hydrogen peroxide). After the reaction was carried out at room temperature for 15 minutes, 20 µL of 2N HCl was added to stop the reaction, and absorbance at 450 nm was determined using a plate reader (TECAN).

DNA Sequencing

The clones positive in the ELISA analysis were analyzed for DNA sequences. Each ELISA-positive clone was cultured, and the plasmid was prepared (QIAprep Spin Mini-Prep kit: QIAGEN) for DNA sequencing. The sequencing primer used was pET-MALseqF: (SEQ ID NO:15: CCA-GAAAGGTGAAATCATGCCGAACATC).

Expression and Purification of Antigen-Binding Clone

Each clone found to have binding activity was inoculated to 200 mL of a 2xYT medium containing ampicillin (50 µg/mL final concentration), and cultured at 37° C. for 3-5 hours ($OD_{600}$=0.5-0.8), after which IPTG (0.1 mM final concentration) was added, and the cells were cultured at 25° C. overnight. The cultured *Escherichia coli* was recovered using a centrifuge, re-suspended in 60 mL of a Lysis buffer (20 mM Tris HCl, pH 7.5, 500 mM NaCl, 10 mM β-mercaptoethanol, 5 mM $MgSO_4$, 10 U/mL DNase), and disrupted using an ultrasonic disruptor (Bioruptor USD-250). The supernatant was recovered via centrifugation and passed through a 0.22 µm filter, after which affinity purification (AKTA Purifier, GE Healthcare) was performed using MBP-Trap (5 mL×2 vials, GE Healthcare). After the purification, the protein solution was replaced with PBS by buffer exchange using a dialytic membrane. A single band was identified by SDS-PAGE, and the concentration was determined using the BCA protein assay kit (PIERCE).

Comparing the Specific Activities of Antigen-Binding Clones (ELISA)

Each PBS-diluted purified binding clone (500 ng/well) was added to a 384-well plate having an antigen immobilized thereon previously, and the binding specific activities of the binding clones were compared in the same manner as with the above-described ELISA (primary screening ELISA).

Determining the Affinity of Antigen-Binding Clones

The affinity of each purified clone was determined using the BIACORE 3000 system, all operations taking place as directed in Biacore's instruction manual. Immobilization of biotinylated antigen proteins (Erk2 and thioredoxin) onto sensor chips was achieved using the streptavidin-mediated SA sensor chip (Biacore).

Immunoprecipitation Experiment of Recombinant Erk2 Protein with Purified Erk2-Binding Clone Protein HEK293T cells, previously cultured in a 6-well plate, were incubated with the addition of 500 µL of PBS containing 0.1% Triton X-100 and a protease inhibitor cocktail (Roche) at 4° C. for 10 minutes to lyse the cells. The cells were centrifuged at ×10000 g for 10 minutes; the resulting supernatant was used as the cell lysate. 5 µg of the Erk2 protein and 10 µg of an Erk2-binding clone (Erk2 clone N) or a control clone (Trx clone A) were added to 50 µL of the cell lysate. The resulting solution was combined with 40 µl of washed (500 μL of PBS×three times) FLAG M2 Agarose Resin (Sigma), and this mixture was gently stirred by rotation at room temperature. One hour later, the Resin was recovered using the MicroSpin Column (GE Healthcare) and washed with 500 μL of PBS three times, after which 50 μL of the FLAG Peptide solution (500 μg/mL) was added, and the binding complex was eluted at room temperature for 5 minutes. Finally, the supernatant was recovered using the MicroSpin Column (GE healthcare), of which 10 μL was analyzed by SDS-PAGE, and 1 μL by Western blotting. The Western blotting was performed using a 1:1000 dilution of an anti-ERK antibody (Cell Signaling Technology) as the primary antibody and a 1:10000 dilution of an HRP-labeled anti-rabbit IgG antibody (GE Healthcare) and a 1:10000 dilution of an anti-FLAG M2-HRP conjugate (Sigma) as the secondary antibodies. Detection was achieved by a standard method using the ECL advance (GE Healthcare).

Figure 4:
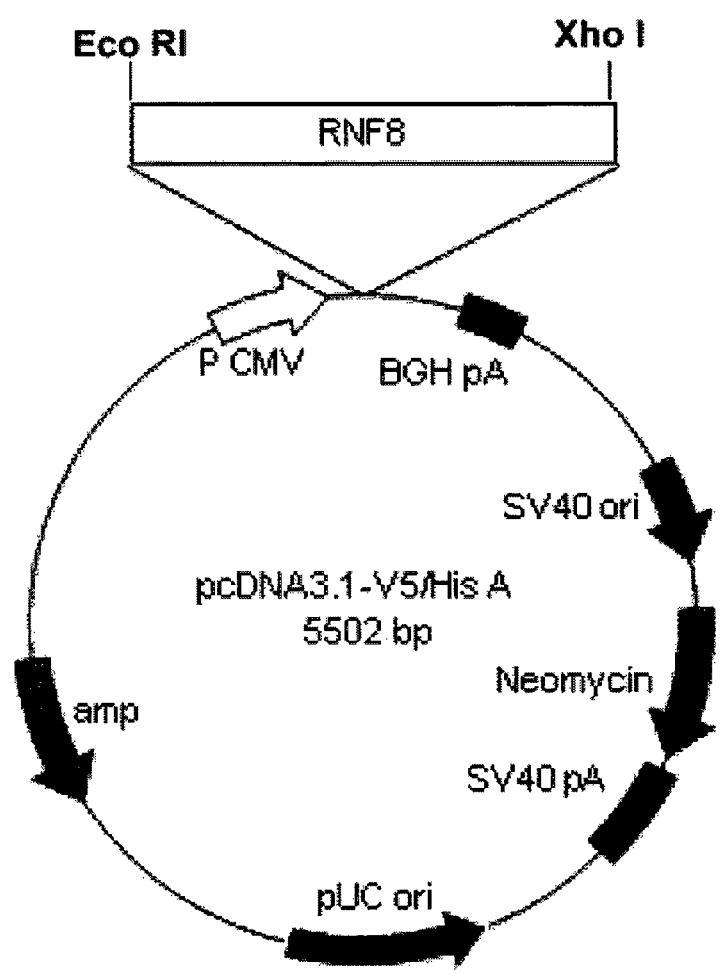
FIG. 4 shows a mammalian cell protein expression vector incorporating the RNF8-FHA gene.

Immunoprecipitation Experiment of Endogenous Erk1/2 with Erk2-Binding Clones Expressed in Mammalian Cells Preparation of pcDNA3.1-RNF8-V5/His Mammalian Cell Expression Plasmid: FIG. 4

A DNA fragment of each clone of RNF8 (Trx clone A, Erk2 clone A, Erk2 clone C, Erk2 clone N) was inserted into the EcoR1/Xho1 site of the expression vector pcDNA3.1-V5/His (Invitrogen), whereby pcDNA3.1-RNF8-V5/His was generated (Sal1 was added to the 3' end of each RNF8 fragment, which was ligated to the vector's Xho1 site). A DNA fragment of each RNF8 clone with a restriction endonuclease site added thereto was prepared by a PCR reaction (KOD Plus DNA polymerase: TOYOBO, denaturation: 94° C., 10 seconds; annealing: 58° C., 30 seconds; elongation: 68° C., 60 seconds; 30 cycles) using a primer set of EcoR1-RNF8-for (SEQ ID NO:16: 5'-gccgaattcac-catgggcgagcctggcttcttcgtc-3') and Sal1-RNF8-rev (SEQ ID NO:17: 5'-gccgtcgacattcttttcaatcatttgatc-3'). Each PCR product was purified using the QIAquick PCR purification kit (QIAGEN), and then treated with the restriction endonuclease. The restriction endonuclease-treated DNA fragment was subjected to 1% agarose gel electrophoresis, and the corresponding band was cut out, and then purified using the MiniElute Gel Extraction Kit (QIAGEN). The purified vector and insert DNA fragments were ligated by a standard method using the TaKaRa Ligation kit Mighty Mix (TaKaRa). The ligation product was transformed into *Escherichia coli* TG1 F—; the resulting colony was cultured; the plasmid was prepared using the QIAprep Spin MiniPrep kit (QIAGEN).

Pulling Down Endogenous ERK1/2 with Expressed Erk2-Binding Clone

HEK293T cells were transfected with pcDNA3.1-RNF8-V5/His on a 6-well plate; 24 hours later, the medium was discarded, 500 μL of PBS containing 0.1% Triton X-100, 10 mM imidazole, and a protease inhibitor cocktail (Roche) was added, and the plate was incubated at 4° C. for 10 minutes to lyze the cells. This was followed by centrifugation at ×10000 g for 10 minutes; the resulting supernatant was used as the cell lysate. 10 μL of the TALON Metal Affinity Resin (TaKaRa) was added to the cell lysate. After incubation at 4° C. for 2 hours, the resin was washed with 500 μL of PBS five times. 20 μL of an SDS-PAGE sample buffer (50 mM Tris-HCl, pH 6.8, 2% SDS, 5% β-mercaptoethanol, 10% glycerol, a small amount of Bromophenol Blue) was added to the washed resin. After boiling this mixture, 10 μL was used as the Western blotting analytical sample. Western blotting was performed using a 1:1000-diluted anti-ERK antibody (Cell Signaling Technology) as the primary antibody, and a 1:10000-diluted HRP-labeled anti-rabbit IgG antibody (GE Healthcare) as the secondary antibody. Detection was achieved by a standard method using the ECL advance (GE Healthcare).

Figure 5:
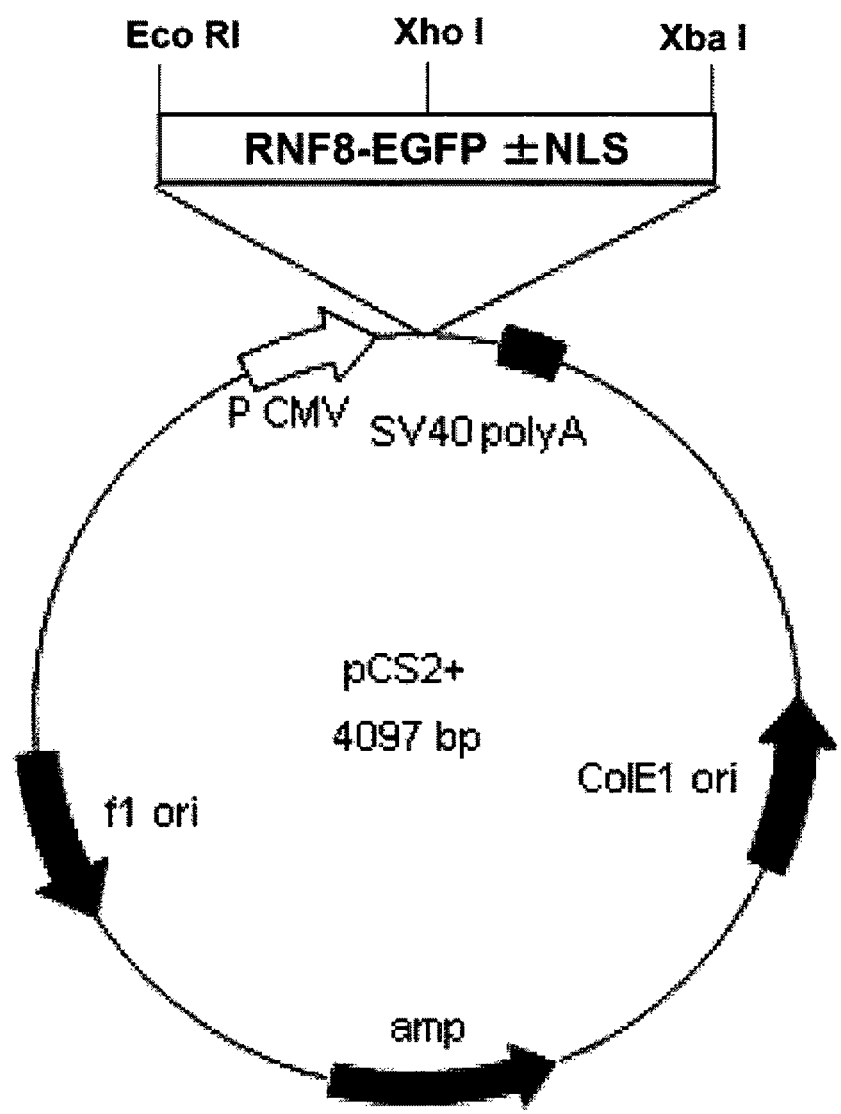
FIG. 5 shows a mammalian cell protein expression vector incorporating the RNF8-FHA gene and the EGFP gene.

Preparation of pCS2-RNF8-EGFP Mammalian Cell Expression Plasmid: FIG. 5

First, a DNA fragment of EGFP was inserted into the Xho1/Xba1 site of the expression vector pCS2+ to yield a plasmid. Furthermore, a DNA fragment of each clone (Trx clone A, Erk2 clone C, Erk2 clone N) was inserted into the EcoR1/Xho1 site of this plasmid, whereby pCS2-RNF8-EGFP was generated (Sal1 was added to the 3' end of each RNF8 fragment, which was ligated to the vector's Xho1 site). A DNA fragment of EGFP with a restriction endonuclease site added thereto and a DNA fragment of each RNF8 clone with a restriction endonuclease site added thereto were prepared by a PCR reaction (KOD Plus DNA polymerase: TOYOBO, denaturation: 94° C., 10 seconds; annealing: 58° C., 30 seconds; elongation: 68° C., 60 seconds; 30 cycles) using a primer set of Xho1-EGFP-for (SEQ ID NO:18: 5'-gccctcgaggtgagcaagggcgaggagctg-3') and Xba1-EGFP-rev (SEQ ID NO:19: 5'-gcctctagattacttgtacagctcgtccat-3') or a primer set of EcoR1-RNF8-for (SEQ ID NO:16: 5'-gccgaattcaccatgggcgagcctggcttcttcgtc-3') and Sal1-RNF8-rev (SEQ ID NO:17: 5'-gccgtcgacattcttttcaatcatttgatc-3'), respectively. Each PCR product was purified using the QIAquick PCR purification kit (QIAGEN) and then treated with the restriction endonuclease. The restriction endonuclease-treated DNA fragment was subjected to agarose electrophoresis and purified using the MiniElute Gel Extraction Kit (QIAGEN). The purified vector and insert DNA fragments were ligated by a standard method using the TaKaRa Ligation kit Mighty Mix (TaKaRa). The ligation product was transformed into *Escherichia coli* TG1 F—; the colony obtained was cultured; the plasmid was prepared using the QIAprep Spin MiniPrep kit (QIAGEN).

Next, a DNA fragment with a nuclear localization signal (NLS) from the SV40 large T antigen added to the C-terminus of EGFP was inserted into the Xho1/Xba1 site of the expression vector pCS2+ to construct a plasmid. Furthermore, a DNA fragment of each clone of RNF8 (Trx clone A, Erk2 clone A, Erk2 clone C, Erk2 clone N) was inserted into the EcoR1/Xho1 site of this plasmid, whereby pCS2-RNF8-EGFP-NLS was generated (Sal1 was added to the 3' end of each RNF8 fragment, which was ligated to the vector's Xho1 site). A DNA fragment of EGFP-NLS with a restriction endonuclease site added thereto and a DNA fragment of each RNF8 clone with a restriction endonuclease site added thereto were prepared by a PCR reaction (KOD Plus DNA polymerase: TOYOBO, denaturation: 94° C., 10 seconds; annealing: 58° C., 30 seconds; elongation: 68° C., 60 seconds; 30 cycles) using a primer set of Xho1-EGFP-for (SEQ ID NO:18: 5'-gccctcgaggtgagcaagggcgaggagctg-3') and Xba1-EGFP-NLS-rev (SEQ ID NO:20: 5'-gcctctagat-cataccttgcgcttcttctttggcggcttgtacagctcgtccatgcc-3') or a primer set of EcoR1-RNF8-for (SEQ ID NO:16: 5'-gccgaattcaccatgggcgagcctggcttcttcgtc-3') and Sal1-RNF8-rev (SEQ ID NO:17: 5'-gccgtcgacattcttttcaatcatttgatc-3'), respectively. The restriction endonuclease-treated DNA fragment was subjected to agarose electrophoresis and purified using the MiniElute Gel Extraction Kit (QIAGEN). The purified vector and insert DNA fragments were ligated by a standard method using the TaKaRa Ligation kit Mighty Mix (TaKaRa). The ligation product was transformed into *Escherichia coli* TG1 F—; the resulting colony was cultured; the plasmid was prepared using the QIAprep Spin MiniPrep kit (QIAGEN).

Expression of RNF8 Artificial Antibody in Mammalian Cells

A mammalian cell line in culture, HEK293T, was cultured in DMEM (Sigma) supplemented with 10% FCS at 37° C. in the presence of a supply of 5% $CO_2$. The cells were transfected with pCS2-RNF8-EGFP or pCS2-RNF8-EGFP-NLS by a standard method using Lipofectamin (Invitrogen) and the plus reagent (Invitrogen).

Experiments of Inhibition of Intracellular Erk2 Phosphorylation Activity with Erk2 Antigen-Binding Clone HEK293T cells were transfected with pCS2-RNF8-EGFP using a 24-well plate; 24 hours later, PMA was added at a final concentration of 100 nM, and the plate was incubated at 37° C. for 30 minutes. After the PMA treatment of the cells, the medium was immediately discarded, and 100 µL of an SDS-PAGE sample buffer (50 mM Tris-HCl pH 6.8, 2% SDS, 5% β-mercaptoethanol, 10% glycerol, a small amount of Bromophenol Blue) was added to lyze the cells. After boiling this lysate, 15 µL was used as the Western blotting analytical sample. The primary antibodies used were anti-p90RSK (Cell Signaling Technology), anti-phosphorylated Ser380 p90RSK (Cell Signaling Technology), anti-phosphorylated Tre359/Ser363 p90RSK (Cell Signaling Technology), and anti-phosphorylated Tre573 p90RSK (Cell Signaling Technology), all of which were used at a dilution rate of 1:1000. The secondary antibody used was an HRP-labeled anti-rabbit IgG antibody (GE Healthcare), used in a 1:10000 dilution. Detection was achieved by a standard method using the ECL Advance (GE Healthcare).

Examination for Intracellular Localization of RNF8 Artificial Antibody and Erk1 and Erk2 (Erk1/2)

After 24 hours of transfection with pCS2-RNF8-EGFP-NLS, HEK293T cells were immobilized with 4% PFA by incubation at room temperature for 15 minutes, after which they were washed with 500 µL of PBS three times. After adding 500 µL of 0.2% Triton X-100/PBS, the cells were incubated at room temperature for 5 minutes for a membrane permeation treatment, and the plate was washed with 500 µL of PBS three times. Next, 500 µL of 10% FCS/PBS was added, and blocking was performed at room temperature for 30 minutes. To stain Erk1/2, a first reaction was carried out at room temperature for 1 hour using an anti-ERK antibody (Cell Signaling) as the primary antibody in a 1:50 diluted solution in 10% FCS/PBS, and the plate was washed with 500 µL of PBS three times. A second reaction was carried out at room temperature for 1 hour using an Alexa555-labeled anti-rabbit IgG antibody (Invitrogen) as the secondary antibody in a 1:500 diluted solution in 10% FCS/PBS, and the plate was washed with PBS three times. Finally, PBS supplemented with Hoechst 33342 was added, and triple staining images for EGFP(RNFB), ERK and the nucleus were examined using a fluorescence microscope (OLYMPUS IX70).

Results and Discussion

Sequencing the Selected Antigen-Binding Proteins

Results of a first screening. ELISA after in vitro selection by ribosome display are shown in Table 1.

TABLE 1

| antigen (protein) | Hit | efficiency |
|---|---|---|
| Erk2 | 89/95 | 93.7% |
| Trx | 34/95 | 35.8% |

Good results were obtained with both antigens (Erk2, Trx), with Erk2 yielding positive clones at a probability of nearly 90%. These positive clones were subjected to DNA sequencing to determine the enriching efficiency on the positive clones. With Erk2, a total of 14 clones with different sequences were obtained, of which about 70% were identified as clones belonging to the group A. Here, the clones belonging to the groups A to M had exactly the same amino acid sequence from Loop 1 to Loop 3, with different sequences in Loop 4 only (Table 2, the sequences of groups A to N correspond to SEQ ID NO:21 to 34, respectively).

TABLE 2

| GROUP | YIELD | loop1 | loop2 | loop3 | loop4 |
|---|---|---|---|---|---|
| A | 64 | FGT | YLPSWFTY | SLT | GIWSDL |
| B | 4 | FGT | YLPSWFTY | SLT | ALKQSL |
| C | 3 | FGT | YLPSWFTY | SLT | AMTTSY |
| D | 3 | FGT | YLPSWFTY | SLT | SHKWWV |
| E | 1 | FGT | YLPSWFTY | SLT | ETGLEW |
| F | 1 | FGT | YLPSWFTY | SLT | SMRHML |
| G | 1 | FGT | YLPSWFTY | SLT | SLPGLA |
| H | 1 | FGT | YLPSWFTY | SLT | LVAYGA |
| I | 1 | FGT | YLPSWFTY | SLT | SLAANL |
| J | 1 | FGT | YLPSWFTY | SLT | SLREXS |
| K | 1 | FGT | YLPSWFTY | SLT | EDRFGL |
| L | 1 | FGT | YLPSWFTY | SLT | AMFSDV |
| M | 1 | FGT | YLPSWFTY | SLT | ALRCRL |
| N | 6 | WGG | GYLWQRRT | VLG | LRSLLL |

This tendency was also observed in case of Trx (Table 3, the sequences of the groups A to H correspond to SEQ ID NO:35 to 42, respectively). Of these eight different clones, the groups A, C, D, E, and F had the same sequence from Loop 1 to Loop 3. These results suggest that the artificial antibody of the present invention may recognize its targets primarily using Loop 1 to Loop 3.

TABLE 3

| GROUP | YIELD | loop1 | loop2 | loop3 | loop4 |
|---|---|---|---|---|---|
| A | 27 | FVP | VLFAEKNA | VWN | QVSPLG |
| B | 1 | FVP | VLFAEKKA | IWN | QVSPLG |
| C | 1 | FVP | VLFAEKNA | VWN | GVFRKG |
| D | 1 | FVP | VLFAEKNA | VWN | RGCLGL |
| E | 1 | FVP | VLFAEKNA | VWN | DPVAVR |
| F | 1 | FVP | VLFAEKNA | VWN | GPQVVC |
| G | 1 | FLP | PMRREKNM | VRI | QVSPLG |
| H | 1 | SDW | RWLGNVVF | AGH | EPSSLH |

To compare the specific binding activities of various clones selected, clones found more than once (groups A, B, C, D, and N) and a solitary clone (group J) from the Erk2-binding clone, and Trx-binding clones (groups A, C, D, G, and H) were expressed and purified. For almost all of these clones, good to yields were obtained with finally purified amounts of about 200-250 mg/L (2xYT medium).

Next, all of the purified binding clones, prepared at 500 ng/well, were compared in terms of binding activity by ELISA (Table 4).

TABLE 4

| Erk2 | | Trx | |
|---|---|---|---|
| Clone | ELISA (S/N) | Clone | ELISA (S/N) |
| A | 30.0 | A | 30.5 |
| B | 30.0 | C | 4.4 |
| C | 12.0 | D | 4.7 |
| D | 13.6 | G | 22.2 |
| J | 25.6 | H | 5.7 |
| N | 12.6 | | |

With Erk2, a remarkable difference in specific activity was observed between the groups A, B, and J and the groups C and D despite the fact that the groups A, B, C, D, and J had the same amino acid sequence from Loop 1 to Loop 3. Trx produced similar results; of the groups A, C, and D, which had the same amino acid sequence from Loop 1 to Loop 3, the groups C and D exhibited remarkably lower specific activity. These results suggest that the Loop 4 of the artificial antibody of the present invention may largely influence the affinity for targets.

Determination of the Affinity of Erk2-Binding Clone

Figure 6:
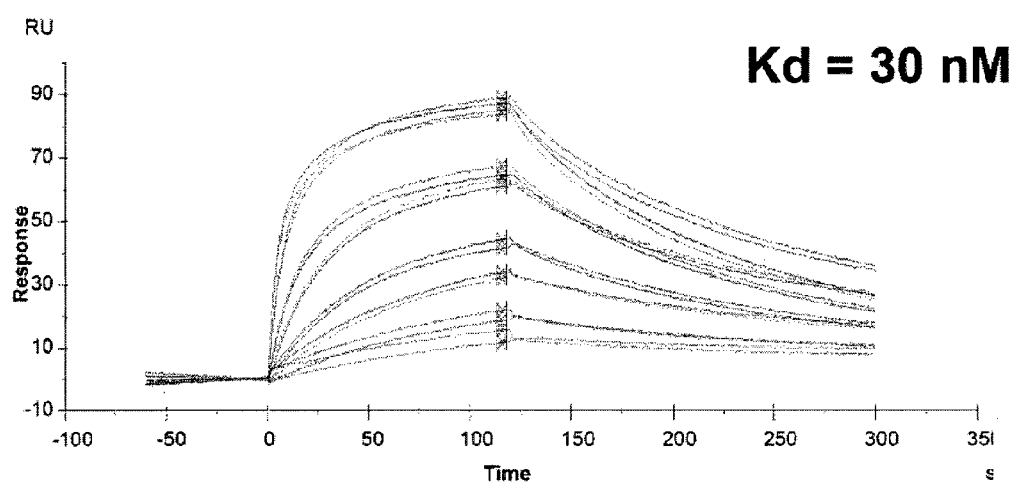
FIG. 6 shows results of a determination of the affinity of Erk2-binding molecules using SPR.

Analysis of the affinity of an Erk2-binding clone (clone N) using SPR (BIACORE) demonstrated that the clone have an affinity equivalent to that of general antibodies with Kd=30 nM (FIG. 6).

Immunoprecipitation of Recombinant Erk2 with Purified Erk2-Binding Clone

Figure 7:
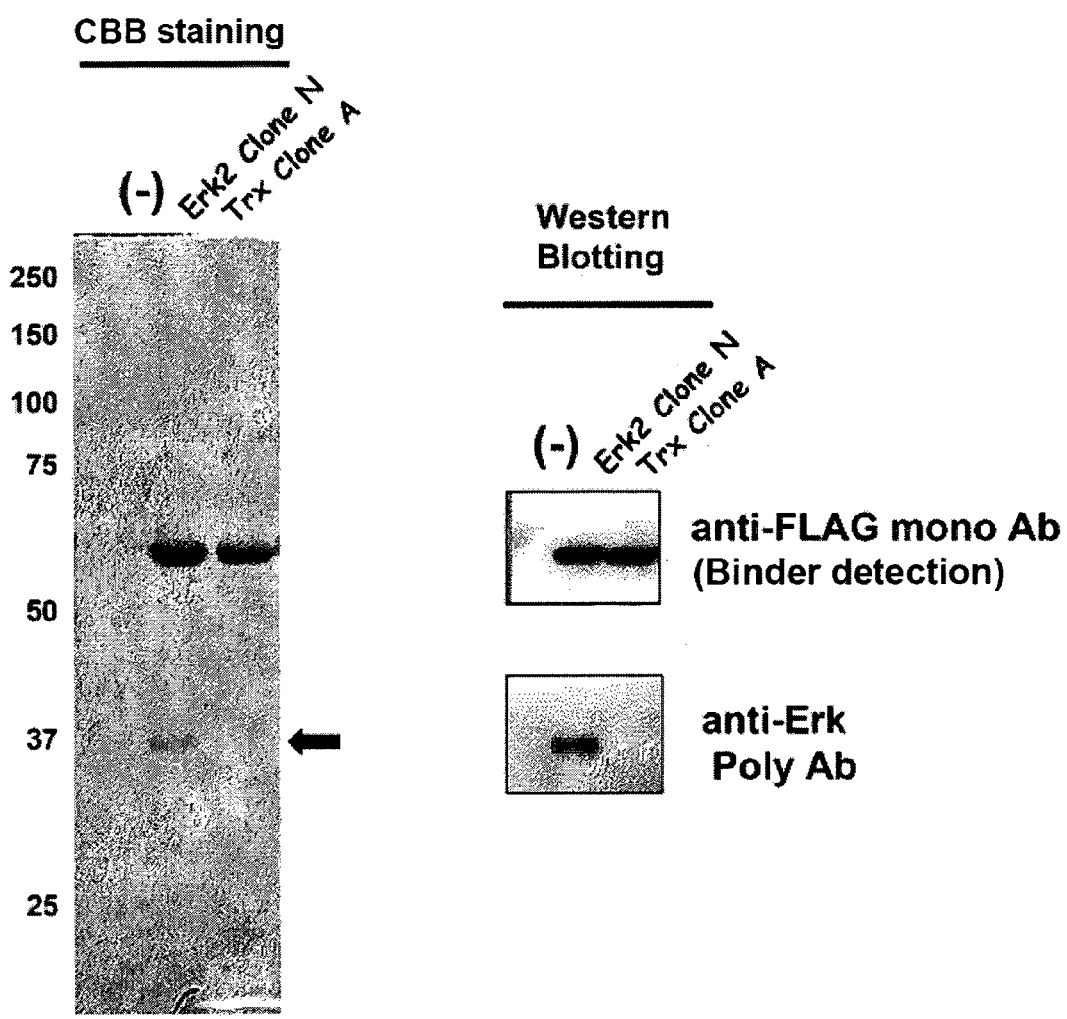
FIG. 7 shows results of an immunoprecipitation experiment of recombinant Erk2 with a purified Erk2-binding clone.

To determine the antigen specificity of a purified Erk2-binding clone (Clone N), the recombinant Erk2 protein was added to mammalian cell extract, and an immunoprecipitation experiment with the Erk2-binding clone was performed (FIG. 7). First, results of SDS-PAGE showed that when adding the Erk2-binding clone, a single band appeared at the position corresponding to the molecular weight of the Erk2 protein, with no other nonspecific band detected. Results of Western blotting identified the detected band as the Erk2 protein. These results demonstrate that the Erk2-binding clone accurately recognizes the Erk2 protein in the cell extract.

Figure 8:
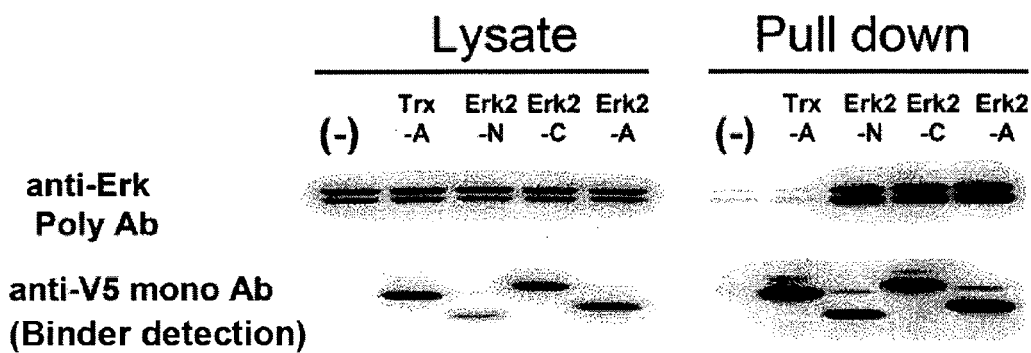
FIG. 8 shows results of Western blotting of endogenous Erk2 by an Erk2-binding clone expressed in mammalian cells.

Immunoprecipitation of Endogenous Erk with Erk2-Binding Clone Expressed in Mammalian Cells Next, in place of an immunoprecipitation experiment with the purified protein, the gene of the Erk2-binding clone was introduced into cells, and the immunoprecipitation of endogenous Erk1 and Erk2 (Erk1/2) was examined (FIG. 8). When the Erk2-binding clone gene was introduced, bands of endogenous Erk1/2 were clearly detected, whereas no band was detected in cells incorporating the control Trx-binding clone gene.

This result demonstrates that the RNF8 artificial antibody is stably expressed in cells and possesses high functionality. Generally, immunoprecipitation is implemented by disrupting cells with a surfactant and the like, and adding a purified antibody protein to the cell extract. In this method, it is necessary to purify the antibody for each subject target, so that the throughput is extremely low. Additionally, because the immunoprecipitation is from cell extract, no results reflecting a more naturalistic intracellular environment can be obtained. The RNF8 artificial antibody of the present invention doesn't have these problems, and in addition affords a totally new method of immunoprecipitation befitting different cell conditions (cell cycle, drug administration and the like).

Figure 9:
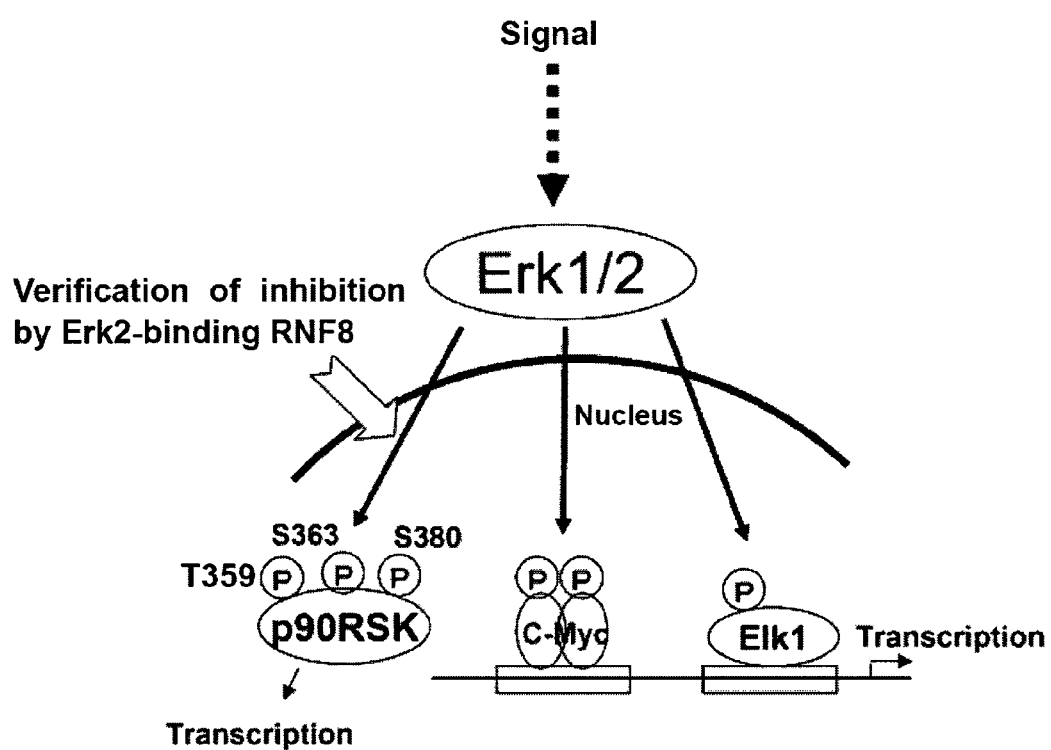
FIG. 9 shows how Erk1/2 functions in cells.
Figure 10:
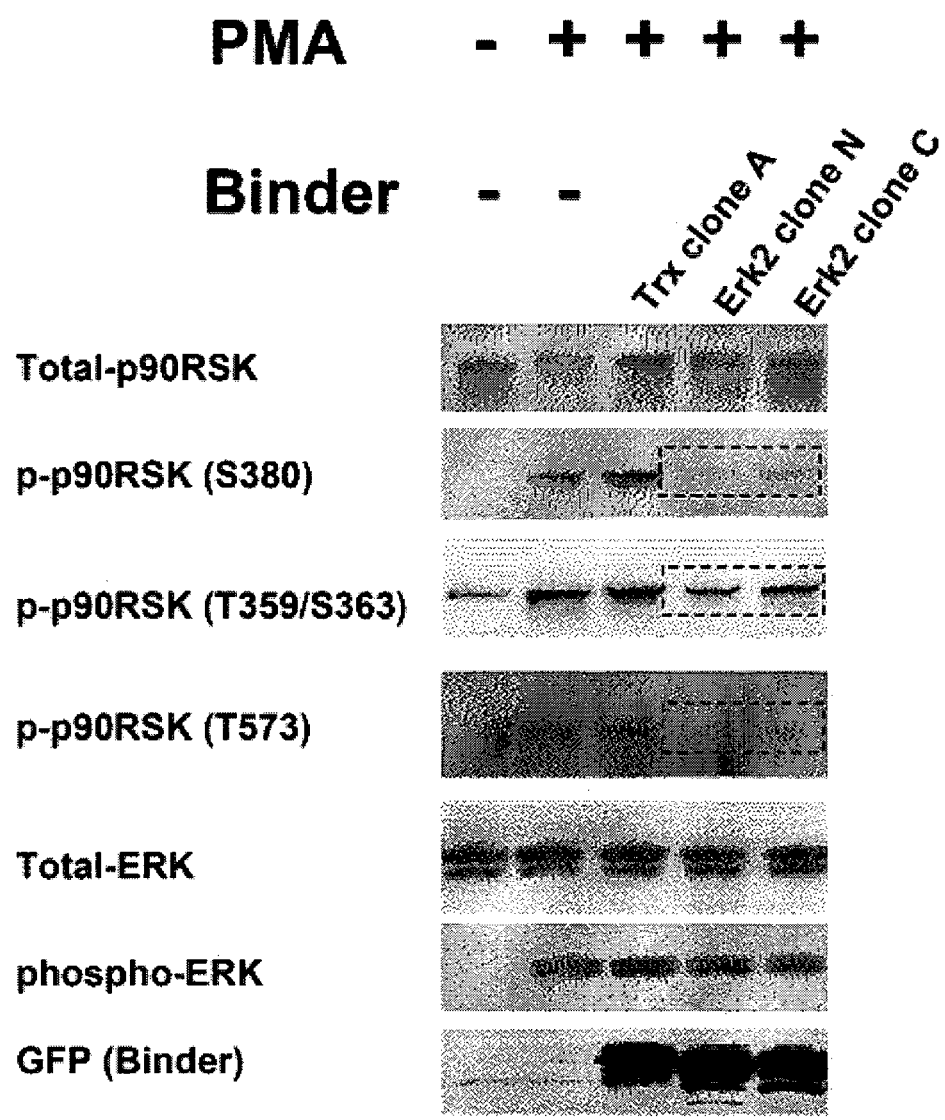
FIG. 10 shows the inhibition of endogenous Erk signals by Erk2-binding clones.

Experiment of Inhibition of Intracellular Erk2 Phosphorylation Activity with Erk2 Antigen-Binding Clone As shown in FIG. 9, Erk1 and Erk2 (Erk1/2) are signaling factors for the phosphorylation of p90RSK, C-Myc, and Elk1. With this in mind, an experiment was performed to determine whether the Erk2-binding, clone are capable of inhibiting the interaction with p90RSK (inhibition of p90RSK phosphorylation) by binding to Erk (FIG. 10).

As a result, introduction of the Erk2-binding RNF8 artificial polypeptide resulted in the detection of a remarkable suppression of p90RSK phosphorylation, confirming that the RNF8 artificial antibody potently inhibits the activity of Erk in cells; extremely high functionality as an intrabody was demonstrated. Many proteins deemed causal factors of a wide variety of diseases that cannot be tackled with general antibody therapeutics are known to be present in cells, therefore, the RNF8 artificial antibody can be applied not only to basic research but also development of novel therapeutics targeting these proteins.

Control of Localization of Endogenous Erk with Erk2-Binding Polypeptide

Figure 11:
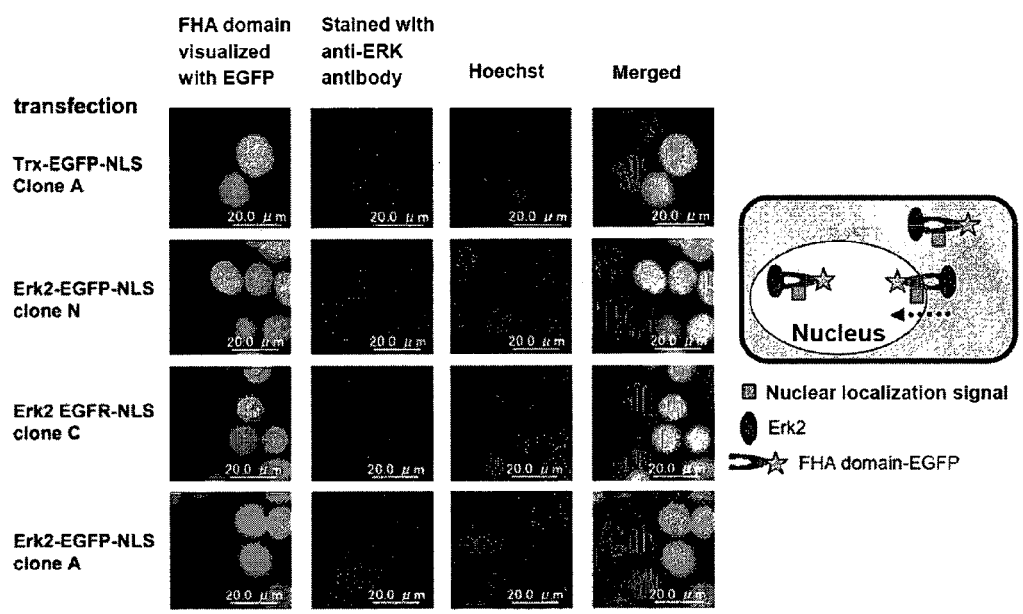
FIG. 11 shows the control of localization of endogenous Erk2 with Erk2-binding clone-NLS (nuclear localization signal).

A nuclear localization signal (NLS) was introduced into Erk2-binding clones, these were expressed in cells, and localization of endogenous Erk was examined (FIG. 11). First, EGFP was examined. Localization in the nuclei of all these binding clones was observed. Next, endogenous Erk was examined using an anti-Erk antibody. All the cells incorporating an Erk2-binding clone exhibited nuclear localization of endogenous Erk, whereas the cells incorporating the control Trx-binding molecule did not exhibit nuclear localization of endogenous Erk.

This result confirmed the nuclear colocalization of endogenous Erk in the cytoplasm by Erk2-binding polypeptides, demonstrating that the intracellular localization of target proteins can be controlled as intended. It is known that in case of an antibody-based intrabody, the localization of the intrabody to the ER can be controlled by adding an ER-retention signal (SEKDEL) [Marasco et al., Proc. Natl. Acad. Sci. USA (1993), vol. 90, pp. 7889-7893]; by adding certain localization signals to the RNF8 artificial antibody (nuclear exporting signal: NES, nucleolar localization signal: NOS, mitochondrial matrix targeting signal: MTS, peroxisomal targeting signal: PTS and the like), it is possible to control the localization to various regions (sometimes as a target complex).

Free Text of Sequence Listing
SEQ ID NO:2 oligonucleotide
SEQ ID NO:3 oligonucleotide
SEQ ID NO:4 oligonucleotide
n stands for any bases.
s stands for guanine or citocine.
SEQ ID NO:5 oligonucleotide
n stands for any bases.
s stands for guanine or citocine.
SEQ ID NO:6 oligonucleotide
n stands for any bases.
s stands for guanine or citocine.
SEQ ID NO:7 oligonucleotide
SEQ ID NO:10 oligonucleotide
SEQ ID NO:11 oligonucleotide
SEQ ID NO:12 oligonucleotide
SEQ ID NO:13 oligonucleotide
SEQ ID NO:14 oligonucleotide SEQ ID NO:15 oligonucleotide
SEQ ID NO:16 oligonucleotide
SEQ ID NO:17 oligonucleotide
SEQ ID NO:18 oligonucleotide
SEQ ID NO:19 oligonucleotide
SEQ ID NO:20 oligonucleotide
SEQ ID NO:21 protein
SEQ ID NO:22 protein
SEQ ID NO:23 protein
SEQ ID NO:24 protein
SEQ ID NO:25 protein
SEQ ID NO:26 protein
SEQ ID NO:27 protein
SEQ ID NO:28 protein
SEQ ID NO:29 protein
SEQ ID NO:30 protein
SEQ ID NO:31 protein
SEQ ID NO:32 protein
SEQ ID NO:33 protein
SEQ ID NO:34 protein
SEQ ID NO:35 protein
SEQ ID NO:36 protein
SEQ ID NO:37 protein
SEQ ID NO:38 protein
SEQ ID NO:39 protein
SEQ ID NO:40 protein
SEQ ID NO:41 protein
SEQ ID NO:42 protein

INDUSTRIAL APPLICABILITY

The method of the present invention for producing an RNF8-FHA domain-modified protein can be utilized in, for example, the biochemical industry and the pharmaceutical industry.

This application is based on a patent application No. 2010-159227 filed in Japan (filing date: Jul. 14, 2010), the contents of which are incorporated in full herein.

---

The invention claimed is:

1. A method of producing an artificial antibody against a predetermined antigen, comprising:
   (i) preparing a RNF8-FHA domain library comprising randomized-loop polypeptides obtained by randomizing two or more of the following loops (a') to (d') in the E3 ubiquitin ligase RNF8-FHA domain comprising the amino acid sequence of SEQ ID NO:1:
   (a') a loop consisting of the 41st-46th amino acid residues of the RNF8 protein shown by SEQ ID NO:1,
   (b') a loop consisting of the 49th-62nd amino acid residues of the RNF8 protein shown by SEQ ID NO:1,
   (c') a loop consisting of the 78th-83rd amino acid residues of the RNF8 protein shown by SEQ ID NO:1,
   (d') a loop consisting of the 108th-118th amino acid residues of the RNF8 protein shown by SEQ ID NO:1,
   wherein each of the randomized-loop polypeptides comprises the amino acid sequence shown by SEQ ID NO:1 except that a random sequence is introduced into two or more loops selected from the group consisting of (a') to (d'), and no amino acid residues are deleted from, substituted for, inserted into, or added to any regions of the amino acid sequence other than loops (a'), (b'), (c'), and (d'), and
   (ii) selecting a randomized-loop polypeptide that binds to the antigen as the artificial antibody from among the randomized-loop polypeptides of the RNF8-FHA domain polypeptide library,
   wherein unmodified RNF8-FHA domain has substantially no binding affinity for the antigen.

2. The method according to claim 1, wherein the number of amino acid residues in the random sequence is 3-12 residues.

3. The method according to claim 2, wherein selecting a randomized-loop polypeptide that binds to the antigen from the randomized-loop polypeptides is performed by in vitro selection.

4. The method according to claim 1, wherein selecting a randomized-loop polypeptide that binds to the antigen from the randomized-loop polypeptides is performed by in vitro selection.

5. The method according to claim 1, wherein the random sequence is introduced into the two or more loops in each of the randomized-loop polypeptides by replacing a region in each of the loops with the random sequence, wherein the region and the random sequence have the same number of amino acid residues.

6. The method according to claim 1, wherein the random sequence is introduced into the two or more loops in each of the randomized-loop polypeptides by replacing each of the loops with the random sequence.

7. The method according to claim 2, wherein the random sequence is introduced into the two or more loops in each of the randomized-loop polypeptides by replacing a region in each of the loops with the random sequence, wherein the region and the random sequence have the same number of amino acid residues.

8. The method according to claim 2, wherein the random sequence is introduced into the two or more loops in each of the randomized-loop polypeptides by replacing each of the loops with the random sequence.

* * * * *

SEQUENCE LISTING

```
<160> NUMBER OF SEQ ID NOS: 42

<210> SEQ ID NO 1
<211> LENGTH: 146
<212> TYPE: PRT
<213> ORGANISM: Homo sapiens

<400> SEQUENCE: 1

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Arg Gly Phe Gly Val Thr Tyr Gln
        35                  40                  45

Leu Val Ser Lys Ile Cys Pro Leu Met Ile Ser Arg Asn His Cys Val
    50                  55                  60

Leu Lys Gln Asn Pro Glu Gly Gln Trp Thr Ile Met Asp Asn Lys Ser
65                  70                  75                  80

Leu Asn Gly Val Trp Leu Asn Arg Ala Arg Leu Glu Pro Leu Arg Val
                85                  90                  95

Tyr Ser Ile His Gln Gly Asp Tyr Ile Gln Leu Gly Val Pro Leu Glu
            100                 105                 110

Asn Lys Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 2
<211> LENGTH: 137
<212> TYPE: DNA
<213> ORGANISM: Artificial Sequence
<220> FEATURE:
<223> OTHER INFORMATION: Synthetic oligonucleotide

<400> SEQUENCE: 2
gactataaag atgacgatga caaaggcgag cctggcttct tcgtcaccgg agaccgcgcc      60
ggtggccgct catggtgcct gcgccgcgtg ggcatgagcg ccggctggct gcttctcgag     120
```

```
gatggttgcg aagttac                                              137

<210> SEQ ID NO 3
<211> LENGTH: 113
<212> TYPE: DNA
<213> ORGANISM: Artificial Sequence
<220> FEATURE:
<223> OTHER INFORMATION: Synthetic oligonucleotide

<400> SEQUENCE: 3
ccgaagaaga ctgggaaacc atttatcctt gtcttagccc taagaatgat caaatgattg   60
aaaagaatga attcggtggc agcggaggtg aatatcaagg ccaatcgtct gac         113

<210> SEQ ID NO 4
<211> LENGTH: 123
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(123)
<223> OTHER INFORMATION: n stands for any bases.
      s stands for guanine or cytosine.

<400> SEQUENCE: 4
cttctcgagg atggttgcga agttaccgtt ggtnnsnnsn nsggtgtcac ctaccagctg   60
gtatcaaaan nsnnsnnsnn snnsnnsnns nnsaaccact gcgttcttaa gcaaaatcct  120
gag                                                                123

<210> SEQ ID NO 5
<211> LENGTH: 127
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(127)
<223> OTHER INFORMATION: n stands for any bases.
      s stands for guanine or cytosine.

<400> SEQUENCE: 5
ccactgcgtt cttaagcaaa atcctgaggg ccaatggacc attatggaca acaagnnsnn   60
snnsggtgtt tggctgaacc gagcgcgcct ggaacctttg cgcgtctata gcattcatca  120
gggtgac                                                            127

<210> SEQ ID NO 6
<211> LENGTH: 117
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(117)
<223> OTHER INFORMATION: n stands for any bases.
      s stands for guanine or cytosine.

<400> SEQUENCE: 6
gcgcgtctat agcattcatc agggtgacta catccaactt ggtnnsnnsn nsnnsnnsnn   60
sgagaatgcc gagtatgaat atgaagttac cgaagaagac tgggaaacca tttatcc    117

<210> SEQ ID NO 7
```

```
<211> LENGTH: 112
<212> TYPE: DNA
<213> ORGANISM: Artificial Sequence
<220> FEATURE:
<223> OTHER INFORMATION: Synthetic oligonucleotide

<400> SEQUENCE: 7
gaaattaata cgactcacta tagggagacc acaacggttt ccctctagaa ataattttgt      60
ttaactttaa gaaggagata taccaatgga ctataaagat gacgatgaca aa             112

<210> SEQ ID NO 8
<211> LENGTH: 24
<212> TYPE: DNA
<213> ORGANISM: Bacteriophage M13K07

<400> SEQUENCE: 8
gaatatcaag gccaatcgtc tgac                                            24

<210> SEQ ID NO 9
<211> LENGTH: 108
<212> TYPE: DNA
<213> ORGANISM: Bacteriophage M13K07

<400> SEQUENCE: 9
ctcgagttat tcattaggtg aggcgttgag ggccagcacg gatgccttgc gcctggctta     60
tccagacggg cgtgctgaat tttgcgccgg aaacgtcacc aatgaaac                 108

<210> SEQ ID NO 10
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 10
gaaattaata cgactcacta tagggagacc acaacggttt ccctctag                  48

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 11
ggattagtta ttcattaggt gaggcgttga gg                                   32

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
gtcagacgat tggccttgat attc                                            24

<210> SEQ ID NO 13
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 13
```
ccgaattcga ctataaagat gacgatgaca aaggc                    35

<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 14
ggaagcttat tcttttcaat catttgatca ttc                      33

<210> SEQ ID NO 15
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 15
ccagaaaggt gaaatcatgc cgaacatc                            28

<210> SEQ ID NO 16
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 16
gccgaattca ccatgggcga gcctggcttc ttcgtc                   36

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 17
gccgtcgaca ttcttttcaa tcatttgatc                          30

<210> SEQ ID NO 18
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 18
gccctcgagg tgagcaaggg cgaggagctg                          30

<210> SEQ ID NO 19
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 19
gcctctagat tacttgtaca gctcgtccat                          30

<210> SEQ ID NO 20
<211> LENGTH: 57
<212> TYPE: DNA

```
<213> ORGANISM: Artificial Sequence
<220> FEATURE:
<223> OTHER INFORMATION: Synthetic oligonucleotide

<400> SEQUENCE: 20
gcctctagat cataccttgc gcttcttctt tggcggcttg tacagctcgt ccatgcc          57

<210> SEQ ID NO 21
<211> LENGTH: 146
<212> TYPE: PRT
<213> ORGANISM: Artificial Sequence
<220> FEATURE:
<223> OTHER INFORMATION: Synthetic protein

<400> SEQUENCE: 21

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Gly Ile Trp Ser
            100                 105                 110

Asp Leu Glu Asn Ala Glu Tyr Glu Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 22
<211> LENGTH: 146
<212> TYPE: PRT
<213> ORGANISM: Artificial Sequence
<220> FEATURE:
<223> OTHER INFORMATION: Synthetic protein

<400> SEQUENCE: 22

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Ala Leu Lys Gln
            100                 105                 110
```

Ser Leu Glu Asn Ala Glu Tyr Glu Tyr Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 23
<211> LENGTH: 146
<212> TYPE: PRT
<213> ORGANISM: Artificial Sequence
<220> FEATURE:
<223> OTHER INFORMATION: Synthetic protein

<400> SEQUENCE: 23

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Ala Met Thr Thr
            100                 105                 110

Ser Tyr Glu Asn Ala Glu Tyr Glu Tyr Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 24
<211> LENGTH: 146
<212> TYPE: PRT
<213> ORGANISM: Artificial Sequence
<220> FEATURE:
<223> OTHER INFORMATION: Synthetic protein

<400> SEQUENCE: 24

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Ser His Lys Trp
            100                 105                 110

```
Trp Val Glu Asn Ala Glu Tyr Glu Val Thr Glu Glu Asp Trp
        115                 120                 125

Glu Thr Ile Tyr Pro Cys Leu Ser Pro Lys Asn Asp Gln Met Ile Glu
        130                 135                 140

Lys Asn
145

<210> SEQ ID NO 25
<211> LENGTH: 146
<212> TYPE: PRT
<213> ORGANISM: Artificial Sequence
<220> FEATURE:
<223> OTHER INFORMATION: Synthetic protein

<400> SEQUENCE: 25

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Glu Thr Gly Leu
            100                 105                 110

Glu Trp Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
        130                 135                 140

Lys Asn
145

<210> SEQ ID NO 26
<211> LENGTH: 146
<212> TYPE: PRT
<213> ORGANISM: Artificial Sequence
<220> FEATURE:
<223> OTHER INFORMATION: Synthetic protein

<400> SEQUENCE: 26

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Ser Met Arg His
```

```
              100                 105                 110
Met Leu Glu Asn Ala Glu Tyr Glu Tyr Glu Val Thr Glu Glu Asp Trp
            115                 120                 125

Glu Thr Ile Tyr Pro Cys Leu Ser Pro Lys Asn Asp Gln Met Ile Glu
        130                 135                 140

Lys Asn
145

<210> SEQ ID NO 27
<211> LENGTH: 146
<212> TYPE: PRT
<213> ORGANISM: Artificial Sequence
<220> FEATURE:
<223> OTHER INFORMATION: Synthetic protein

<400> SEQUENCE: 27

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Ser Leu Pro Gly
            100                 105                 110

Leu Ala Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 28
<211> LENGTH: 146
<212> TYPE: PRT
<213> ORGANISM: Artificial Sequence
<220> FEATURE:
<223> OTHER INFORMATION: Synthetic protein

<400> SEQUENCE: 28

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95
```

```
Tyr Ser Ile His Gln Gly Asp Tyr Ile Gln Leu Gly Leu Val Ala Tyr
            100                 105                 110

Gly Ala Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 29
<211> LENGTH: 146
<212> TYPE: PRT
<213> ORGANISM: Artificial Sequence
<220> FEATURE:
<223> OTHER INFORMATION: Synthetic protein

<400> SEQUENCE: 29

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
            85                  90                  95

Tyr Ser Ile His Gln Gly Asp Tyr Ile Gln Leu Gly Ser Leu Ala Ala
            100                 105                 110

Asn Leu Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 30
<211> LENGTH: 146
<212> TYPE: PRT
<213> ORGANISM: Artificial Sequence
<220> FEATURE:
<223> OTHER INFORMATION: Synthetic protein
<220> FEATURE:
<221> NAME/KEY: misc_feature
<222> LOCATION: (113)..(113)
<223> OTHER INFORMATION: Xaa can be any naturally occurring amino acid

<400> SEQUENCE: 30

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Gly Thr Gly Val Thr Tyr Gln
        35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
```

```
                65                  70                  75                  80
Leu Thr Gly Val Trp Leu Asn Arg Ala Arg Leu Glu Pro Leu Arg Val
                    85                  90                  95

Tyr Ser Ile His Gln Gly Asp Tyr Ile Gln Leu Gly Ser Leu Arg Glu
                100                 105                 110

Xaa Ser Glu Asn Ala Glu Tyr Glu Tyr Glu Val Thr Glu Glu Asp Trp
                115                 120                 125

Glu Thr Ile Tyr Pro Cys Leu Ser Pro Lys Asn Asp Gln Met Ile Glu
    130                 135                 140

Lys Asn
145

<210> SEQ ID NO 31
<211> LENGTH: 146
<212> TYPE: PRT
<213> ORGANISM: Artificial Sequence
<220> FEATURE:
<223> OTHER INFORMATION: Synthetic protein

<400> SEQUENCE: 31

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
                20                  25                  30

Asp Gly Cys Glu Val Thr Val Gly Phe Gly Thr Gly Val Thr Tyr Gln
                35                  40                  45

Leu Val Ser Lys Tyr Leu Pro Ser Trp Phe Thr Tyr Asn His Cys Val
    50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                    85                  90                  95

Tyr Ser Ile His Gln Gly Asp Tyr Ile Gln Leu Gly Glu Asp Arg Phe
                100                 105                 110

Gly Leu Glu Asn Ala Glu Tyr Glu Tyr Glu Val Thr Glu Glu Asp Trp
                115                 120                 125

Glu Thr Ile Tyr Pro Cys Leu Ser Pro Lys Asn Asp Gln Met Ile Glu
    130                 135                 140

Lys Asn
145

<210> SEQ ID NO 32
<211> LENGTH: 146
<212> TYPE: PRT
<213> ORGANISM: Artificial Sequence
<220> FEATURE:
<223> OTHER INFORMATION: Synthetic protein

<400> SEQUENCE: 32

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
                20                  25                  30

Asp Gly Cys Glu Val Thr Val Gly Phe Gly Thr Gly Val Thr Tyr Gln
                35                  40                  45

Leu Val Ser Lys Tyr Leu Pro Ser Trp Phe Thr Tyr Asn His Cys Val
    50                  55                  60
```

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Ala Met Phe Ser
            100                 105                 110

Asp Val Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 33
<211> LENGTH: 146
<212> TYPE: PRT
<213> ORGANISM: Artificial Sequence
<220> FEATURE:
<223> OTHER INFORMATION: Synthetic protein

<400> SEQUENCE: 33

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
                20                  25                  30

Asp Gly Cys Glu Val Thr Val Gly Phe Gly Thr Gly Val Thr Tyr Gln
            35                  40                  45

Leu Val Ser Lys Tyr Leu Pro Ser Trp Phe Thr Tyr Asn His Cys Val
50                  55                  60

Leu Lys Gln Asn Pro Glu Gly Gln Trp Thr Ile Met Asp Asn Lys Ser
65                  70                  75                  80

Leu Thr Gly Val Trp Leu Asn Arg Ala Arg Leu Glu Pro Leu Arg Val
                85                  90                  95

Tyr Ser Ile His Gln Gly Asp Tyr Ile Gln Leu Gly Ala Leu Arg Cys
            100                 105                 110

Arg Leu Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145

<210> SEQ ID NO 34
<211> LENGTH: 146
<212> TYPE: PRT
<213> ORGANISM: Artificial Sequence
<220> FEATURE:
<223> OTHER INFORMATION: Synthetic protein

<400> SEQUENCE: 34

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
                20                  25                  30

Asp Gly Cys Glu Val Thr Val Gly Trp Gly Gly Val Thr Tyr Gln
            35                  40                  45

Leu Val Ser Lys Gly Tyr Leu Trp Gln Arg Arg Thr Asn His Cys Val
50                  55                  60

-continued

Leu Lys Gln Asn Pro Glu Gly Gln Trp Thr Ile Met Asp Asn Lys Val
65                  70                  75                  80

Leu Gly Gly Val Trp Leu Asn Arg Ala Arg Leu Glu Pro Leu Arg Val
            85                  90                  95

Tyr Ser Ile His Gln Gly Asp Tyr Ile Gln Leu Gly Leu Arg Ser Leu
        100                 105                 110

Leu Leu Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
        130                 135                 140

Lys Asn
145

<210> SEQ ID NO 35
<211> LENGTH: 146
<212> TYPE: PRT
<213> ORGANISM: Artificial Sequence
<220> FEATURE:
<223> OTHER INFORMATION: Synthetic protein

<400> SEQUENCE: 35

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Val Pro Gly Val Thr Tyr Gln
        35                  40                  45

Leu Val Ser Lys Val Leu Phe Ala Glu Lys Asn Ala Asn His Cys Val
    50                  55                  60

Leu Lys Gln Asn Pro Glu Gly Gln Trp Thr Ile Met Asp Asn Lys Val
65                  70                  75                  80

Trp Asn Gly Val Trp Leu Asn Arg Ala Arg Leu Glu Pro Leu Arg Val
            85                  90                  95

Tyr Ser Ile His Gln Gly Asp Tyr Ile Gln Leu Gly Gln Val Ser Pro
        100                 105                 110

Leu Gly Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
        130                 135                 140

Lys Asn
145

<210> SEQ ID NO 36
<211> LENGTH: 146
<212> TYPE: PRT
<213> ORGANISM: Artificial Sequence
<220> FEATURE:
<223> OTHER INFORMATION: Synthetic protein

<400> SEQUENCE: 36

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
            20                  25                  30

Asp Gly Cys Glu Val Thr Val Gly Phe Val Pro Gly Val Thr Tyr Gln
        35                  40                  45

Leu Val Ser Lys Val Leu Phe Ala Glu Lys Asn Ala Asn His Cys Val

```
                    50                  55                  60
Leu Lys Gln Asn Pro Glu Gly Gln Trp Thr Ile Met Asp Asn Lys Ile
 65                  70                  75                  80

Trp Asn Gly Val Trp Leu Asn Arg Ala Arg Leu Glu Pro Leu Arg Val
                     85                  90                  95

Tyr Ser Ile His Gln Gly Asp Tyr Ile Gln Leu Gly Gln Val Ser Pro
                100                 105                 110

Leu Gly Glu Asn Ala Glu Tyr Glu Tyr Glu Val Thr Glu Glu Asp Trp
                115                 120                 125

Glu Thr Ile Tyr Pro Cys Leu Ser Pro Lys Asn Asp Gln Met Ile Glu
                130                 135                 140

Lys Asn
145

<210> SEQ ID NO 37
<211> LENGTH: 146
<212> TYPE: PRT
<213> ORGANISM: Artificial Sequence
<220> FEATURE:
<223> OTHER INFORMATION: Synthetic protein

<400> SEQUENCE: 37

Gly Glu Pro Gly Phe Phe Val Thr Gly Asp Arg Ala Gly Gly Arg Ser
 1               5                  10                  15

Trp Cys Leu Arg Arg Val Gly Met Ser Ala Gly Trp Leu Leu Leu Glu
                20                  25                  30

Asp Gly Cys Glu Val Thr Val Gly Phe Val Pro Gly Val Thr Tyr Gln
                35                  40                  45

Leu Val Ser Lys Val Leu Phe Ala Glu Lys Asn Ala Asn His Cys Val
 50                  55                  60

Leu Lys Gln Asn Pro Glu Gly Gln Trp Thr Ile Met Asp Asn Lys Val
 65                  70                  75                  80

Trp Asn Gly Val Trp Leu Asn Arg Ala Arg Leu Glu Pro Leu Arg Val
                     85                  90                  95

Tyr Ser Ile His Gln Gly Asp Tyr Ile Gln Leu Gly Gly Val Phe Arg
                100                 105                 110

Lys Gly Glu Asn Ala Glu Tyr Glu Tyr Glu Val Thr Glu Glu Asp Trp
                115                 120                 125

Glu Thr Ile Tyr Pro Cys Leu Ser Pro Lys Asn Asp Gln Met Ile Glu
                130                 135                 140

Lys Asn
145

<210> SEQ ID NO 38
<211> LENGTH: 146
<212> TYPE: PRT
<213> ORGANISM: Artificial Sequence
<220> FEATURE:
<223> OTHER INFORMATION: Synthetic protein

<400> SEQUENCE: 38

Gly Glu Pro Gly Phe Phe Val Thr Gly Asp Arg Ala Gly Gly Arg Ser
 1               5                  10                  15

Trp Cys Leu Arg Arg Val Gly Met Ser Ala Gly Trp Leu Leu Leu Glu
                20                  25                  30

Asp Gly Cys Glu Val Thr Val Gly Phe Val Pro Gly Val Thr Tyr Gln
                35                  40                  45
```

```
Leu Val Ser Lys Val Leu Phe Ala Glu Lys Asn Ala Asn His Cys Val
 50                  55                  60

Leu Lys Gln Asn Pro Glu Gly Gln Trp Thr Ile Met Asp Asn Lys Val
 65                  70                  75                  80

Trp Asn Gly Val Trp Leu Asn Arg Ala Arg Leu Glu Pro Leu Arg Val
                 85                  90                  95

Tyr Ser Ile His Gln Gly Asp Tyr Ile Gln Leu Gly Arg Gly Cys Leu
                100                 105                 110

Gly Leu Glu Asn Ala Glu Tyr Glu Tyr Glu Val Thr Glu Glu Asp Trp
                115                 120                 125

Glu Thr Ile Tyr Pro Cys Leu Ser Pro Lys Asn Asp Gln Met Ile Glu
    130                 135                 140

Lys Asn
145

<210> SEQ ID NO 39
<211> LENGTH: 146
<212> TYPE: PRT
<213> ORGANISM: Artificial Sequence
<220> FEATURE:
<223> OTHER INFORMATION: Synthetic protein

<400> SEQUENCE: 39

Gly Glu Pro Gly Phe Phe Val Thr Gly Asp Arg Ala Gly Gly Arg Ser
  1               5                  10                  15

Trp Cys Leu Arg Arg Val Gly Met Ser Ala Gly Trp Leu Leu Leu Glu
                 20                  25                  30

Asp Gly Cys Glu Val Thr Val Gly Phe Val Pro Gly Val Thr Tyr Gln
                 35                  40                  45

Leu Val Ser Lys Val Leu Phe Ala Glu Lys Asn Ala Asn His Cys Val
 50                  55                  60

Leu Lys Gln Asn Pro Glu Gly Gln Trp Thr Ile Met Asp Asn Lys Val
 65                  70                  75                  80

Trp Asn Gly Val Trp Leu Asn Arg Ala Arg Leu Glu Pro Leu Arg Val
                 85                  90                  95

Tyr Ser Ile His Gln Gly Asp Tyr Ile Gln Leu Gly Asp Pro Val Ala
                100                 105                 110

Val Arg Glu Asn Ala Glu Tyr Glu Tyr Glu Val Thr Glu Glu Asp Trp
                115                 120                 125

Glu Thr Ile Tyr Pro Cys Leu Ser Pro Lys Asn Asp Gln Met Ile Glu
    130                 135                 140

Lys Asn
145

<210> SEQ ID NO 40
<211> LENGTH: 146
<212> TYPE: PRT
<213> ORGANISM: Artificial Sequence
<220> FEATURE:
<223> OTHER INFORMATION: Synthetic protein

<400> SEQUENCE: 40

Gly Glu Pro Gly Phe Phe Val Thr Gly Asp Arg Ala Gly Gly Arg Ser
  1               5                  10                  15

Trp Cys Leu Arg Arg Val Gly Met Ser Ala Gly Trp Leu Leu Leu Glu
                 20                  25                  30

Asp Gly Cys Glu Val Thr Val Gly Phe Val Pro Gly Val Thr Tyr Gln
                 35                  40                  45
```

```
Leu Val Ser Lys Val Leu Phe Ala Glu Lys Asn Ala Asn His Cys Val
    50                  55                  60

Leu Lys Gln Asn Pro Glu Gly Gln Trp Thr Ile Met Asp Asn Lys Val
65                  70                  75                  80

Trp Asn Gly Val Trp Leu Asn Arg Ala Arg Leu Glu Pro Leu Arg Val
                85                  90                  95

Tyr Ser Ile His Gln Gly Asp Tyr Ile Gln Leu Gly Gly Pro Gln Val
                100                 105                 110

Val Cys Glu Asn Ala Glu Tyr Glu Tyr Glu Val Thr Glu Glu Asp Trp
                115                 120                 125

Glu Thr Ile Tyr Pro Cys Leu Ser Pro Lys Asn Asp Gln Met Ile Glu
130                 135                 140

Lys Asn
145

<210> SEQ ID NO 41
<211> LENGTH: 146
<212> TYPE: PRT
<213> ORGANISM: Artificial Sequence
<220> FEATURE:
<223> OTHER INFORMATION: Synthetic protein

<400> SEQUENCE: 41

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
                20                  25                  30

Asp Gly Cys Glu Val Thr Val Gly Phe Leu Pro Gly Val Thr Tyr Gln
                35                  40                  45

Leu Val Ser Lys Pro Met Arg Arg Glu Lys Asn Met Asn His Cys Val
    50                  55                  60

Leu Lys Gln Asn Pro Glu Gly Gln Trp Thr Ile Met Asp Asn Lys Val
65                  70                  75                  80

Arg Ile Gly Val Trp Leu Asn Arg Ala Arg Leu Glu Pro Leu Arg Val
                85                  90                  95

Tyr Ser Ile His Gln Gly Asp Tyr Ile Gln Leu Gly Gln Val Ser Pro
                100                 105                 110

Leu Gly Glu Asn Ala Glu Tyr Glu Tyr Glu Val Thr Glu Glu Asp Trp
                115                 120                 125

Glu Thr Ile Tyr Pro Cys Leu Ser Pro Lys Asn Asp Gln Met Ile Glu
130                 135                 140

Lys Asn
145

<210> SEQ ID NO 42
<211> LENGTH: 146
<212> TYPE: PRT
<213> ORGANISM: Artificial Sequence
<220> FEATURE:
<223> OTHER INFORMATION: Synthetic protein

<400> SEQUENCE: 42

Gly Glu Pro Gly Phe Phe Val Thr Gly Asp Arg Ala Gly Gly Arg Ser
1               5                   10                  15

Trp Cys Leu Arg Arg Val Gly Met Ser Ala Gly Trp Leu Leu Leu Glu
                20                  25                  30

Asp Gly Cys Glu Val Thr Val Gly Ser Asp Trp Gly Val Thr Tyr Gln
```

```
                35                  40                  45
Leu Val Ser Lys Arg Trp Leu Gly Asn Val Val Phe Asn His Cys Val
    50                  55                  60

Leu Lys Gln Asn Pro Glu Gly Gln Trp Thr Ile Met Asp Asn Lys Ala
65                  70                  75                  80

Gly His Gly Val Trp Leu Asn Arg Ala Arg Leu Glu Pro Leu Arg Val
                85                  90                  95

Tyr Ser Ile His Gln Gly Asp Tyr Ile Gln Leu Gly Glu Pro Ser Ser
            100                 105                 110

Leu His Glu Asn Ala Glu Tyr Glu Tyr Glu Val Thr Glu Glu Asp Trp
        115                 120                 125

Glu Thr Ile Tyr Pro Cys Leu Ser Pro Lys Asn Asp Gln Met Ile Glu
    130                 135                 140

Lys Asn
145
```